United States Patent [19]

Prasher

[11] Patent Number: 5,541,309
[45] Date of Patent: Jul. 30, 1996

[54] MODIFIED APOAEQUORIN HAVING INCREASED BIOLUMINESCENT ACTIVITY

[75] Inventor: Douglas Prasher, Falmouth, Mass.

[73] Assignee: Woods Hole Oceanographic Institution (WHOI), Woods Hole, Mass.

[21] Appl. No.: 331,379

[22] Filed: Oct. 28, 1994

Related U.S. Application Data

[62] Division of Ser. No. 982,650, Dec. 1, 1992, Pat. No. 5,360,728.

[51] Int. Cl.$^6$ .......................... C12N 15/12; C12N 15/53
[52] U.S. Cl. ...................................... 536/23.2; 536/23.5
[58] Field of Search .................................. 536/23.2, 23.5

[56] References Cited

U.S. PATENT DOCUMENTS

| | | | |
|---|---|---|---|
| 4,396,579 | 8/1983 | Schroeder et al. | 436/546 |
| 4,604,364 | 8/1986 | Kosak | 436/501 |
| 5,093,240 | 3/1992 | Inouye et al. | 435/69.1 |
| 5,139,937 | 8/1992 | Inouye et al. | 435/69.1 |
| 5,162,227 | 11/1992 | Cormier | 435/69.1 |
| 5,288,623 | 2/1994 | Zenno et al. | 435/69.7 |
| 5,422,266 | 6/1995 | Cormier et al. | 435/252.3 |

OTHER PUBLICATIONS

Tsuji, F. I. et al., "Site-specific mutagenesis of the calcium-binding photoprotein aequorin," *Proc. Natl. Acad. Sci. USA*, vol. 83, pp. 8107–8111, (Nov. 1986).

Crowl, R. et al., "Versatile expression vectors for high-level synthesis of cloned products in *Escherichia coli*," *Gene*, Vol. 38, pp. 31–38, (1985).

Bernard, H. et al., "Use of the Phage Promoter PL to Promote Gene Expression in Hybrid Plasmid Cloning Vehicles," *Methods of Enzymology*, vol. 68, pp. 482–492 (1979).

Lewis, M. et al., "Efficient site directed *in vitro* mutagenesis using ampicillin selection," *Nucleic Acids Research*, vol. 18, No. 12, pp. 3439–3444, (1990).

Prasher, D. C. et al., "Cloning and Expression of the cDNA Coding for Aequorin, a Bioluminescent Calcium–Binding Protein," *Biochemical and Biophysical Research Communications*, vol. 126, No. 3, pp. 1259–1268, (Feb. 15, 1985).

Inouye, S. et al., "Expression of Apoaequorin Complementary DNA in *Escherichia coli*," *Biochemistry*, vol. 25, No. 26, pp. 8425–8429, (Dec. 30, 1986).

Inouye, S., et al., "Cloning and sequence analysis of cDNA for the luminescent protein aequorin," *Proc. Natl. Acad. Sci. USA*, vol. 82, pp. 3154–3158, (May 1985).

Charbonneau, H. et al., "Amino Acid Sequence of the Calcium–Dependent Photoprotein Aequorin," *American Chemical Society*, vol. 24, No. 24, pp. 6762–6771, (Nov. 19, 1985).

Shimomura, O. et al., "Resistivity to denaturation of the apoprotein of aequorin and reconstitution of the luminescent photoprotein from the partially denatured apoprotein," *Biochem. J.*, vol. 199, pp. 825–828, (Dec. 1981).

Prendergast, F. G. et al., "Chemical and Physical Properties of Aequorin and the Green Fluorescent Protein Isolated from *Aequorea forskalea*," *American Chemical Society*, vol. 17, No. 17, pp. 3448–3453, (Aug. 1978).

Ward, W. W. et al., "Extraction of *Renilla*–type luciferin from the calcium–activated photoproteins aequorin, mnemiopsin, and berovin," *Proc. Nat. Acad. Sci. USA*, vol. 72, No. 7, pp. 2530–2534, (Jul. 1975).

Shimomura, O. et al., "Chemical Nature of Bioluminescence Systems in Coelenterates," *Proc. Nat. Acad. Sci. USA*, vol. 72, No. 4, pp. 1546–1549, (Apr. 1975).

(List continued on next page.)

*Primary Examiner*—Stephen G. Walsh
*Attorney, Agent, or Firm*—Jones & Askew

[57] ABSTRACT

The present invention encompasses modified apoaequorin nucleotide and amino acid sequences capable of emitting light in the presence of luciferin and a light-triggering cation such as $Ca^{2+}$, which possess bioluminescent activity greater than unmodified apoaequorin and methods of use therefore.

9 Claims, 4 Drawing Sheets

OTHER PUBLICATIONS

Patel, A. et al., "Calcium–Sensitive Photoproteins as Bioluminescent Labels in Immunoassay," *Analytical Applications of Bioluminescence and Chemiluminescence*, pp. 273–276, (1984).

Stephenson, D. G. et al., "Studies on the Luminescent Response of the $Ca^{2+}$–Activated Photoprotein, Obelin," *Biochimica et Biophysica Acta*, vol. 678, pp. 65–75, (1981).

Cormier, M. J., "Renilla and Aequorin Bioluminescence," *Bioluminescence and Chemiluminescence*, pp. 225–233, (1985).

Cormier, M. J., "Mechanism of energy conversion and transfer in bioluminescence," *Chemical Abstract*, vol. 93, No. 5, p. 545, Abstract No. 4201h, (Aug. 4, 1980).

DeLuca, M. A., "Bioluminescence and Chemiluminescence," *Methods in Enzymology*, vol. LVII, pp. 238–590, (1979).

Hart, R. C. et al., "Mechanism of the Enzyme–Catalyzed Bioluminescent Oxidation of Coelenterate–Type Luciferin," *Biochemical and Biophysical Research Communications*, vol. 81, No. 3, pp. 980–986, (Apr. 14, 1978).

Cormier, M. J., "Comparative Biochemistry of Animal Systems," *Bioluminescence In Action*, Academic Press, pp. 75–108, (1978).

Cormier, M. J. et al., "Evidence for Similar biochemical Requirements for Bioluminescence among the Coelenterates," *Journal of Cellular Physiology*, vol. 81, No. 2, pp. 291–297, (Apr. 1973).

Patel, A. et al., "A new chemiluminescent label for use in immunoassay," *Biochemical Society Transactions*, vol. 10, pp. 224–225, (1982).

Blinks, J. R. et al., "Practical Aspects of the Use of Aequorin as a Calcium Indicator: Assay, Preparation, Microinjection, and Interpretation of Signals," *Methods of Enzymology*, vol. 57, pp. 292–328, (1978).

Cormier, M. J., et al., "Bioluminescence: Recent Advances," *Annual Review of Biochemistry*, vol. 44, pp. 255–271, (1975).

Prasher, D. C. et al., "Sequence Comparisons of cDNAs Encoding for Aequorin Isotypes," *Biochemistry*, American Chemical Society, pp. 1326–1332, (1987).

"Bioluminescence Technology," *The Genesis Report/DX*, vol. 1, No. 5, pp. 8–15, (Feb./Mar. 1992).

MODIFIED APOAEQUORIN HAVING INCREASED BIOLUMINESCENT ACTIVITY

This a division of application Ser. No. 07/982,650, filed Dec. 1, 1992 now U.S. Pat No. 5,360,728.

FIELD OF THE INVENTION

This invention relates to the field of genetic engineering, and more particularly to the modified apoaequorin genes coding for apoaequorin having altered bioluminescent activity, and to the production of modified apoaequorin having altered bioluminescent activity by expression of altered apoaequorin genes in microorganisms.

DESCRIPTION OF THE BACKGROUND

Apoaequorin is a single polypeptide chain protein which can be isolated from the luminous jellyfish *Aequorea victoria*. When this protein contains one molecule of coelenterate luciferin bound non-covalently to it, it is known as aequorin. Aequorin is oxidized in the presence of calcium ions to produce visible light. Once light is produced, the spent protein (apoaequorin) can be purified from the oxidized luciferin and subsequently recharged using natural or synthetic luciferin under appropriate conditions. The addition of calcium ions to the recharged aequorin will again result in the production of light. Apoaequorin can therefore be used in various chemical and biochemical assays as a marker.

Natural apoaequorin is not a single compound but rather represents a mixture of microheterogeneous molecular species. When pure natural aequorin, representing that of many thousands of individual Aequorea, is subjected to electrophoresis (O. Gabriel, *Methods Enzymol.* (1971)22:565–578) in alkaline buffers under non-denaturing conditions, at least six distinct bands of blue luminescence are visible when the gel is immersed in 0.1M $CaCl_2$. This observation agrees with that of J. R. Blinks et al. (*Fed. Proc.* (1975) 34:474) who observed as many as twelve luminescent bands after the isoelectric focusing of a similar extract. Blinks et al. observed more species because isoelectric focusing is capable of higher resolution than is electrophoresis. However, none of the bands was ever isolated as a pure polypeptide.

Furthermore, it is difficult to produce sufficient aequorin or apoaequorin from jellyfish or other natural sources to provide the amounts necessary for use in bioluminescence assays. Accordingly, an improved means for producing apoaequorin in sufficient quantities for commercial utilization is greatly needed.

Known molecular biology and recombinant DNA techniques permit one skilled in the art to synthesize a protein or peptide normally made by another organism. These techniques make use of a fundamental relationship which exists in all living organisms between the genetic material, usually DNA, and the proteins synthesized by the organism. This relationship is such that the amino acid sequence of the protein is reflected in the nucleotide sequence of the DNA. There are one or more trinucleotide sequence groups specifically related to each of the twenty amino acids most commonly occurring in proteins. As a consequence, the amino acid sequence of every protein or peptide is reflected by a corresponding nucleotide sequence, according to a well understood relationship. Furthermore, this sequence of nucleotides can, in principle, be translated by any living organism.

In its basic outline, a method of endowing a microorganism with the ability to synthesize a new protein involves three general steps: (1) isolation and purification (or chemical synthesis) of the specific gene or nucleotide sequence containing the genetically coded information for the amino acid sequence of the desired protein, (2) recombination of the isolated nucleotide sequence with an appropriate vector, typically the DNA of a bacteriophage or plasmid, and (3) transfer of the vector to the appropriate microorganism and selection of a strain of the recipient microorganism containing the desired genotype.

The symbols and abbreviations used herein are set forth in the following table.

TABLE 1

| | |
|---|---|
| DNA, deoxyribonucleic acid | A—Adenine |
| RNA, ribonucleic acid | T—Thymine |
| cDNA, complementary DNA (enzymatically synthesized from an mRNA sequence) | G—Guanine |
| | C—Cytosine |
| mRNA, messenger RNA | U—Uracil |
| | Tris-2-Amino-2 hydroxymethyl 1,3-propanediol |
| dATP, deoxyadenosine triphosphate | |
| dGTP, deoxyguanosine triphosphate | |
| dCTP, deoxycytidine triphosphate | EDTA, ethylene diamine tetraacetic acid |
| TCA—Trichloroacetic acid | |
| dTTP—thymidine triphosphate | ATP—adenosine triphosphate |

Restriction endonucleases are enzymes capable of hydrolyzing phosphodiester bonds in DNA, thereby creating a break in the continuity of the DNA strand. The principal feature of a restriction enzyme is that its hydrolytic action is exerted only at a point where a specific nucleotide sequence occurs. Such a sequence is termed the restriction site for the restriction endonuclease. When acting on double-stranded DNA, some restriction endonucleases hydrolyze the phosphodiester bonds on both strands at the same point, producing blunt ends. Others catalyze hydrolysis of bonds separated by a few nucleotides from each other, producing free single stranded regions at each end of the cleaved molecule. Such single-stranded ends are self-complementary, hence cohesive, and may be used to rejoin the hydrolyzed DNA. Since any DNA susceptible to cleavage by such an enzyme must contain the same recognition site, the same cohesive ends will be produced, so that it is possible to join heterogeneous sequences of DNA which have been treated with restriction endonuclease to other sequences similarly treated.

Tsuji, et al., (1986) *Proc. Natl. Acad. Sci. USA* 83:8107–8111, disclose specific mutations in the aequorin amino acid sequence. However, Tsuji, et al. conducted their studies on the 189 amino acid fragment of aequorin, which is missing the first seven amino acids of the protein. Their experiments were designed to investigate the role of putative $Ca^{2+}$ binding sites in the protein, the three cysteines, and a histidine in the hydrophobic region. Each of the mutants generated resulted in aequorin having activity below that of fully regenerated unmodified 189 amino acid aequorin fragment. See Tsuji, et al. Table 2. What is needed, however, is modified aequorin proteins having greater activity than naturally occurring or unmodified recombinantly produced aequorin.

SUMMARY OF THE INVENTION

It is an object of this invention, therefore, to provide a microorganism capable of providing useful quantities of homogeneous modified apoaequorin.

It is a further object of this invention to provide a recombinant DNA vector capable of being inserted into a microorganism and expressing modified apoaequorin.

It is still another object of this invention to provide a DNA segment of defined structure that can be produced synthetically that can be used in the production of the desired recombinant DNA vectors.

It is yet another object of this invention to provide a peptide that can be produced synthetically in a laboratory or by microorganism that will possess increased activity relative to unmodified aequorin.

It is yet another object of the invention to provide altered apoaequorin gene sequences.

It is yet another object of the invention to provide apoaequorin genes having site-directed point mutations.

It is yet another object of the present invention to provide homogeneous altered apoaequorin having greater specific activity than native apoaequorin or unaltered recombinant apoaequorin.

These and other objects of the invention as will hereinafter become more readily apparent have been accomplished by providing homogeneous modified proteins of apoaequorin peptide capable of emitting light in the presence of luciferin and a divalent cation such as $Ca^{2+}$, and having increased bioluminescent activity relative to naturally occurring or recombinantly produced apoaequorin.

The modified apoaequorin proteins of the present invention are produced by making mutations in the genetic sequence or alterations in the amino acid sequence of an apoaequorin sequence. Examples of apoaequorin sequences that may be modified include the complete 196 amino acid recombinant apoaequorin, and a 189 amino acid bioluminescent fragment, identified as SEQ ID NO: 1 and SEQ ID NO: 2, respectively, and shown below.

Specific examples of modified apoaequorins possessing greater bioluminescent activity than unmodified apoaequorin include proteins having the sequence of SEQ ID NO: 1 and SEQ ID NO: 2, where aspartate 124 is changed to serine, glutamate 135 is changed to serine, or glycine 129 is changed to alanine. Sequences of modified complete 196 amino acid apoaequorins, SEQ ID NO: 3, SEQ ID NO:4, and SEQ ID NO:5. SEQ ID NO: 3, Asp 124 is changed to Ser. SEQ ID NO: 4, Glu 135 is changed to Ser. SEQ ID NO: 5, Gly 129 is changed to Ala.

The modified sequences of the present invention further encompass specific variations in amino acids at disclosed positions of microheterogeneity, conservative amino acid substitutions, degenerate codon replacements, or changes in non-essential residues, that result in functional modified apoaequorin having increased bioluminescent activity relative to unmodified apoaequorin.

BRIEF DESCRIPTION OF THE FIGURES

The accompanying figures and drawings are provided to demonstrate the results obtained in the specific examples which illustrate the invention but are not considered to be limiting thereof.

DESCRIPTION OF THE PREFERRED EMBODIMENTS

Figure 1:
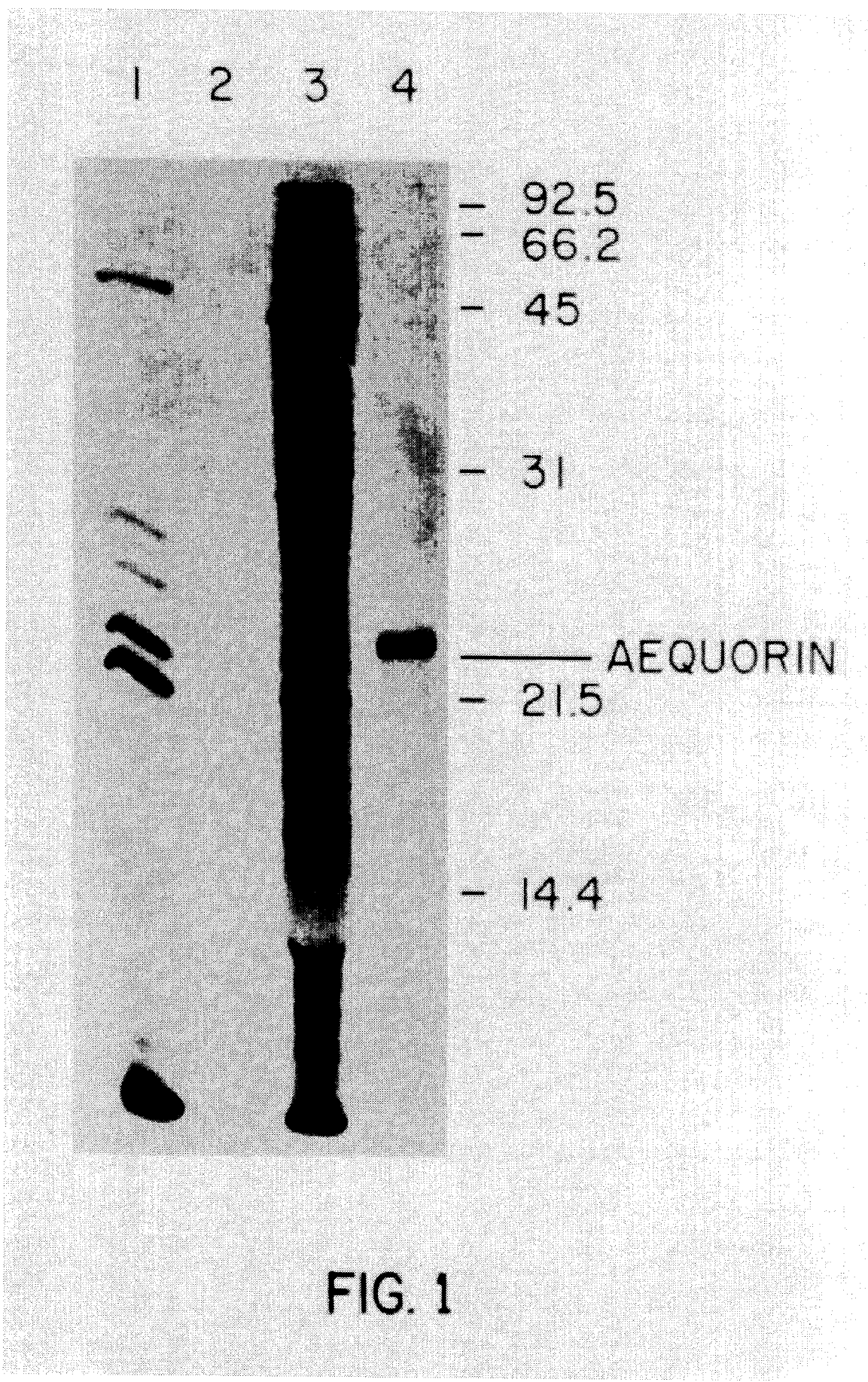
FIG. 1 is a photograph showing an autoradiographic analysis of in vitro translated proteins using poly(A+)RNA isolated from Aequorea Jellyfish. The translation was performed in the absence (lane 1) of presence (lane 3) of Aequorea Poly(A+)RNA. The anti-aequorin immunoprecipitated proteins from the two reactions were applied to lanes 2 and 4, respectively. On the right are marked the positions of the protein molecular weight standards phosphorylase b, BSA, ovalbumin, carbonic anhydrase, SBTI and lysozyme. The position of native aequorin is also indicated.

The present invention encompasses recombinant DNA vectors capable of expressing the protein apoaequorin in a microorganism and the amino acid sequence of apoaequorin, thereby providing access to homogeneous apoaequorin. Additionally, the present invention encompasses modifications in the apoaequorin gene sequence such that the modified genes encode an apoaequorin having altered bioluminescent activity relative to unmodified apoaequorin. In a preferred embodiment, the modified apoaequorin possesses bioluminescent activity that is greater than that of unmodified apoaequorin. Genetic alterations may be accomplished by, for example, site-directed mutagenesis. Some mutant apoaequorin gene sequences coding for apoaequorin protein having altered bioluminescent activity are disclosed as examples.

Aequorin is thought to bind calcium at three binding sites located between amino acids 31 (asp) to 42 (glu), 124 (asp) to 135 (glu), and 160 (asp) to 17 1 (glu), respectively. The amino acid numbering system used designates the first amino acid in the coding sequence (met) as amino acid number 1, as opposed to the numbering system of Charbonneau, et al. (1985), based on the purified native aequorin, where the seventh amino acid (val) is designated as amino acid number 1.

SEQ ID NO: 1 is the subject of U.S. patent application Ser. No. 07/960,195, filed Oct. 9, 1992 now U.S. Pat. No. 5,422,266. Of course, as will be obvious to one skilled in the art, various degenerate codons can be substituted into SEQ ID NO: 1 that will result in the identical amino acid sequence of SEQ ID NO: 1. All such substitutions of degenerate codons are equivalent because they result in identical amino acid sequences, and are, therefore, encompassed within the scope of the appended claims. The sequence for apoaequorin is subject to significant microheterogeneity where variation in the amino acid and/or nucleotide sequence occurs at specific points in the sequence. Functional apoaequorin proteins may have variations relative to SEQ ID NO: 1 at one or more of the microheterogeneous residues. The positions of microheterogeneity, and the specific variations that occur at each, are shown in Table 2.

TABLE 2

POINTS OF MICROHETEROGENEITY IN THE APOAEQUORIN SEQUENCE.

| Residue | Amino Acid Variations |
| --- | --- |
| 4 | Glu, Lys |
| 12 | Ser, Pro |
| 15 | Asp, Asn |
| 18 | Arg, Lys |
| 37 | Lys, Arg |
| 70 | Glu, Gly |
| 71 | Ala, Asp |
| 85 | Asp, Glu |
| 88 | Glu, Ala |
| 95 | Arg, Lys |
| 98 | Ser, Thr |
| 99 | Glu, Asp, Cys |
| 102 | Lys, Glu |
| 103 | Lys, Arg |
| 105 | Ala, Ser |
| 108 | Glu, Gln |
| 109 | Pro, Ile |
| 114 | Ile, Leu |
| 123 | Val, Ile |
| 132 | Ser, Thr |
| 142 | Ala, Ser |
| 148 | Ser, Thr |
| 157 | Arg, Lys |
| 164 | Ser, Asn |

Naturally derived apoaequorin (i.e. from Aequorea) is a mixture of microheterogeneous forms of the protein. In contrast, the recombinant sequence described in SEQ ID NO: 1, represents a homogeneous apoaequorin when produced in a recombinant expression system. Further, it is known that the 189 amino acid peptide of apoaequorin, shown in SEQ ID NO: 2, containing the sequence from $Val_7$ to $Pro_{196}$ is a functional peptide fragment capable of bioluminescent activity. All of the various substitutions applicable for SEQ ID NO: 1, discussed above, are applicable to SEQ ID NO: 2, with the exception of replacements within the first seven amino acids, including microhetergeneous substitutions at amino acid position 4.

Still further, other minor variations in the apoaequorin amino acid sequence, representing modification at non-essential residues, can be made that will result in functional bioluminescent activity. Non-essential residues are those residues which when altered or modified do not significantly affect the bioluminescent activity of the protein or peptide. Additionally, conservative amino acid substitutions wherein one amino acid is replaced with another amino acid that possesses similar structural and/or physical properties, which are well known to one in the art, can be made such that the resulting peptide or protein retains bioluminescent activity.

Consequently, the modified apoaequorin sequences of the present invention, which will be described in more detail below, may contain additional modifications (1) by substituting at a particular position in the nucleotide sequence degenerate codons which code for the same amino acid, (2) by incorporating specific amino acid substitutions at positions of microheterogeneity, (3) by altering non-essential residues, (4) by making conservative amino acid substitutions, and (5) by removing up to at least the first seven amino acids from the 196 amino acid sequence. Any combination of the above modifications that result in a functional bioluminescent protein having greater activity than unmodified apoaequorin is encompassed within the scope of the invention.

Thus, any modified apoaequorin proteins or peptides that possess the ability to emit light, or DNA molecules that code for a protein or peptide capable of emitting light, and preferably having increased bioluminescent activity relative to unmodified apoaequorin is contemplated as being equivalent to those peptides and DNA molecules that are set forth in more detail, as will be appreciated by those skilled in the art. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the biological activity of the resulting molecule, especially if the replacement does not involve an amino acid at a calcium binding site.

Whether a change in the aequorin nucleotide or amino acid sequence results in a functioning peptide can readily be determined by incubating the resulting peptide with a luciferin followed by contacting it with calcium ions or other light-triggering divalent cations. The assay is fast and simple. Functional peptides will emit light, which is readily measured using known instruments and methods. For example, scintillation counters and photometers (e.g. luminometers), photographic film, and solid state devices such as charge coupled devices, may be used to detect and measure the emission of light. Examples of this process are described later in detail. If the protein emits light, particularly at a higher level of activity than unmodified aequorin, then the nucleotide or amino acid replacement is immaterial, and the protein being tested is equivalent to those discussed herein and thus encompassed within the scope of the appended claims. Peptides in which more than one amino acid or codon replacement has taken place can readily be tested in the same manner and also are contemplated to be within the scope of the claimed invention.

Since the DNA sequence for the apoaequorin gene has been fully identified, including its points of microheterogeneity, it is possible to produce a DNA gene entirely by synthetic chemistry, after which the gene can be inserted into any of the many available DNA vectors using known techniques of recombinant DNA technology. Thus the present invention can be carried out using reagents, plasmids, and microorganisms which are freely available and in the public domain at the time of filing of this patent application.

For example, nucleotide sequences greater than 100 bases long can be readily synthesized. Such oligonucleotides can readily be spliced using, among others, the techniques described later in this application to produce any nucleotide sequence described herein. Furthermore, automated equipment is also available that makes direct synthesis of any of the peptides disclosed herein readily available. Such equipment provides ready access to the peptides of the invention, either by direct synthesis or by synthesis of a series of fragments that can be coupled using other known techniques.

In addition to the specific nucleotides sequences disclosed, DNA (or corresponding RNA) molecules of the invention can have additional nucleotides preceding or following those that are specifically listed. For example, poly A can be added to the 3'-terminus, restriction endonuclease sites can be added to one or both terminus, and transcriptional stop sites can be added to the 3'-terminus. Additionally, DNA molecules containing a promoter region or other control region upstream from the gene can be produced. All DNA molecules containing the sequences of the invention will be useful for at least one purpose since all can minimally be fragmented to produce oligonucleotide probes and be used in the isolation of additional DNA from biological sources.

Peptides of the invention can be prepared as homogeneous preparations, either by direct synthesis or by using a cloned gene as described herein. The term "homogeneous" refers to a peptide or DNA sequence where the primary molecular structure (i.e., the sequence of amino acids or nucleotides) of substantially all molecules present in the composition under consideration is identical. The term "substantially" used in the preceding sentence preferably means at least 95% by weight, more preferably at least 99% by weight, and most preferably at least 99.8% by weight. The presence of fragments derived from entire molecules of the homogeneous peptide or DNA sequence, if present in no more than 5% by weight, preferably 1% by weight, and more preferably 0.2% by weight, is not to be considered in determining homogeneity since the term "homogeneous" relates to the presence of entire molecules (and fragments thereof) having a single defined structure as opposed to mixtures (such as those that occur in natural apoaequorin) in which several molecules of similar molecular weight are present but which differ in their primary molecular structure. The term "isolated" used herein refers to pure peptide, DNA, or RNA separated from other peptides, DNAs, or RNAs, respectively, and being found in the presence of (if anything) only a solvent, buffer, ion or other component normally present in a biochemical solution of the same. "Isolated" does not encompass either natural materials in their native state or natural materials that have been separated into components (e.g., in an acylamide gel) but not obtained either as pure substances or as solutions. The term "pure" used herein preferably has the same numerical limits as "substantially" immediately above. The terms "replaced by" or "replacement" or "changed to" used herein do not necessarily refer to any action that must take place, but rather to the peptide that exists when an indicated "replacement" amino acid is present in the same position as the amino acid indicated to be present in a different formula. The term "bioluminescent" used herein refers to the ability of an apoaequorin protein sequence to bind a light-producing oxidizable cofactor or substrate, such as a luciferin, and emit light in the presence of a light-triggering cation such as $Ca^{2+}$. A luciferin may be either naturally derived luciferin, derivatized luciferin, such as benzyl luciferin, or a synthetically produced luciferin. A preferred luciferin is coelenterate luciferin.

Salts of any of the peptides described herein will naturally occur when such peptides are present in (or isolated from) aqueous solutions of various pits. All salts of peptides having the indicated biological activity are considered to be within the scope of the present invention. Examples include alkali, alkaline earth, and other metal salts of carboxylic acid residues, acid addition salts (e.g., HCl) of amino residues, and zwitterions formed by reactions between carboxylic acid and amino residues within the same molecule.

The present invention also encompasses other minor modifications and alterations in the apoaequorin gene sequence that produce mutant apoaequorin genes which code for altered apoaequorin proteins having increased bioluminescent activity relative to naturally occurring apoaequorin or unmodified recombinantly. For example, modifications may be made wherein one or more codons are deleted from the apoaequorin gene nucleotide sequence causing a corresponding deletion in the amino acid sequence of apoaequorin. Alternatively, one or more codons may be added to the apoaequorin gene nucleotide sequence, causing an addition in the apoaequorin amino acid sequence of one or more amino acids. The modified apoaequorins of the present invention also include modified genes and proteins wherein one or more codons or amino acids are modified so as to increase the bioluminescent activity of the resulting aequorin, where additional other codons or amino acids that do not affect aequorin bioluminescent activity are also modified. Thus, all modified apoaequorin sequences, either nucleotide or amino acid, that result in aequorins having increased bioluminescent activity are encompassed by the present invention. The modifications in the apoaequorin gene nucleotide sequence contemplated above may be accomplished by any of the methods known to one skilled in the art. Examples of such methods include chemical mutagenesis, and site-directed mutagenesis. In a preferred embodiment of the invention, genetic information encoded as mRNA is obtained from Aequorea jellyfish and used in the construction of a cDNA, which is in turn used as a basis to produce the modified DNA sequences and peptides of the invention. It is preferred to use a cell extract from the light emitting organs of an Aequorea jellyfish as a source of mRNA, although a whole body cell extract may be used. Typically, a jellyfish or pans thereof is cut into small pieces (minced) and the pieces are ground to provide an initial crude cell suspension. The cell suspension is sonicated or otherwise treated to disrupt cell membranes so that a crude cell extract is obtained. Known techniques of biochemistry (e.g., preferential precipitation of proteins) can be used for initial purification if desired. The crude cell extract, or a partially purified RNA portion therefrom, is then treated to further separate the RNA. For example, crude cell extract can be layered on top of a 5 ml cushion of 5.7CsCl, 10 mM Tris-HCl, pH 7.5,1 mM EDTA in a 1 in.×3 ½ in. nitrocellulose tube and centfifuged in an SW27 rotor (Beckman Instruments Corp., Fullerton, Calif.) at 27,000 rpm for 16 hrs at 15° C. After centrifugation, the tube contents are decanted, the tube is drained, and the bottom ½ cm containing the clear RNA pellet is cut off with a razor blade. The pellets are transferred to a flask and dissolved in 20 ml 10 mM Tris-HCl, pH 7.5,1 mM EDTA, 5% sarcosyl and 5% phenol. The solution is then made 0.1M in NaCl and shaken with 40 ml of a 1:1 phenol:chloroform mixture. RNA is precipitated from the aqueous phase with ethanol in the presence of 0.2M Nacetate pH 5.5 and collected by centrifugation. Any other method of isolating RNA from a cellular source may be used instead of this method.

Various forms of RNA may be employed such as crude or partially purified messenger RNA (ie., polyadenylated), which may be heterogeneous in sequence and in molecular size. The selectivity of the RNA isolation procedure is enhanced by any method which results in an enrichment of the desired mRNA in the heterodisperse population of mRNA isolated. Any such prepurification method may be employed in preparing a gene of the present invention, provided that the method does not introduce endonucleolytic cleavage of the mRNA.

Prepurification to enrich for desired mRNA sequences may also be carried out using conventional methods for fractionating RNA, after its isolation from the cell. Any technique which does not result in degradation of the RNA may be employed. The techniques of preparative sedimentation in a sucrose gradient and gel electrophoresis are especially suitable.

The mRNA must be isolated from the source cells under conditions which preclude degradation of the mRNA. The action of RNase enzymes is particularly to be avoided because these enzymes are capable of hydrolytic cleavage of the RNA nucleotide sequence. A suitable method for inhibiting RNase during extraction from cells involves the use of 4M guanidium thiocyanate and 1M mercaptoethanol during the cell disruption step. In addition, a low temperature and a pH near 5.0 are helpful in further reducing RNase degradation of the isolated RNA.

Generally, mRNA is prepared essentially free of contaminating protein, DNA, polysaccharides and lipids. Standard methods are well known in the art for accomplishing such purification. RNA thus isolated contains non-messenger as well as messenger RNA. A convenient method for separating the mRNA of eucaryotes is chromatography on columns of oligo-dT cellulose, or other oligonucleotide-substituted column material such as poly U-Sepharose, taking advantage of the hydrogen bonding specificity conferred by the presence of polyadenylic acid on the 3'-end of eucaryotic mRNA.

The next step in most methods is the formation of DNA complementary to the isolated heterogeneous sequences of mRNA. The enzyme of choice for this reaction is reverse transcriptase, although in principle any enzyme capable of forming a faithful complementary DNA copy of the RNA template could be used. The reaction may be carded out under conditions described in the prior art, using mRNA as a template and a mixture of the four deoxynucleoside triphosphates, dATP, dGTP, dCTP, and dTTP, as precursors for the DNA strand. It is convenient to provide that one of the deoxynucleoside triphosphates be labeled with a $^{32}P$ in the alpha position, in order to monitor the course of the reaction, to provide a tag for recovering the product after separation procedures such as chromatography and electrophoresis, and for the purpose of making quantitative estimates of recovery.

The cDNA transcripts produced by the reverse transcriptase reaction are heterogeneous in molecular size due to variations in the initiation and termination points of individual transcripts, relative to the mRNA template. The variability at the 5' end is thought to be due to the fact that the oligo-dT primer used to initiate synthesis is capable of binding at a variety of loci along the polyadenylated region of the mRNA. Synthesis of the cDNA transcript begins at an indeterminate point in the poly-A region, and variable length of poly-A region is transcribed depending on the initial binding site of the oligo-dT primer. It is possible to avoid this indeterminacy by the use of a primer have a unique sequence that is complementary to the region 5' to the poly A tract. This primer will have a preferred and defined binding site for initiating the reverse transcription reaction.

The indeterminacy at the 3'-end of the cDNA transcript is due to a variety of factors affecting the reverse transcriptase reaction, and to the possibility of partial degradation of the RNA template. The isolation of specific cDNA transcripts of maximal length is greatly facilitated if conditions for the reverse transcriptase reaction are chosen which not only favor full length synthesis but also repress the synthesis of small DNA chains. Preferred reaction conditions for avian myeloblastosis virus reverse transcriptase are given in the examples section of U.S. Pat. No. 4,363,877 and are herein incorporated by reference. The specific parameters which may be varied to provide maximal production of long-chain DNA transcripts of high fidelity are reaction temperature, salt concentration, amount of enzyme, concentration of primer relative to template, and reaction time.

The conditions of temperature and salt concentration are chosen so as to optimize specific base-pairing between the oligo-dT primer and the polyadenylated portion of the RNA template. Under properly chosen conditions, the primer will be able to bind at the polyadenylated region of the RNA template, but non-specific initiation due to primer binding at other locations on the template, such as short, A-rich sequences, will be substantially prevented. The effects of temperature and salt are interdependent. Higher temperatures and low salt concentrations decrease the stability of specific base-pairing interactions. The reaction time is kept as short as possible, in order to prevent non-specific initiations and to minimize the opportunity for degradation. Reaction times are interrelated with temperature, lower temperatures requiring longer reaction times. At 42° C., reactions ranging from 1 minutes to 10 minutes are suitable. The primer should be present in 50 to 500 fold molar excess over the RNA template and the enzyme should be present in similar molar excess over the RNA template. The use of excess enzyme and primer enhances initiation and cDNA chain growth so that long-chain cDNA transcripts are produced efficiently within the confines of the sort incubation times.

The cDNA prepared for restriction endonuclease treatment may be radioactively labeled so that it may be detected after subsequent separation steps. A preferred technique is to incorporate a radioactive label such as $^{32}P$ in the alpha position of one of the four deoxynucleoside triphosphate precursors. Highest activity is obtained when the concentration of radioactive precursor is high relative to the concentration of the non-radioactive form. However, the total concentration of any deoxynucleoside triphosphate should be greater than 30 μM, in order to maximize the length of cDNA obtained in the reverse transcriptase reaction. See Efstratiadis, A., Maniatis, T., Kafatos, F. C., Jeffrey, A., and Vournakis, J. N., Cell. (1975) 4:367. For the purpose of determining the nucleotide sequence of cDNA, the 5' ends may be conveniently labeled with $^{32}P$ in a reaction catalyzed by the enzyme polynucleotide kinase.

Prior to restriction endonuclease treatment, cDNA transcripts obtained from most sources will be found to be heterodisperse in length. By the action of a properly chosen restriction endonuclease, or pair of endonucleases, polynucleotide chains containing the desired sequence will be cleaved at the respective restriction sites to yield polynucleotide fragments of uniform length. Upon gel electrophoresis, these will be observed to form a distinct band. Depending on the presence or absence of restriction sites on other sequences, other discrete bands may be formed as well, which will most likely be of different length than that of the desired sequence. Therefore, as a consequence of restriction endonuclease action, the gel electrophoresis pattern will reveal the appearance of discrete bands, while the remainder of the cDNA will continue to be heterodisperse. In the case where the desired cDNA sequence comprises the major polynucleotide species present, the electrophoresis pattern will reveal that most of the cDNA is present in the discrete band.

Although it is unlikely that two different sequences will be cleaved by restriction enzymes to yield fragments of essentially similar length, a method for determining the purity of the defined length fragments is desirable. Sequence analysis of the electrophoresis band may be used to detect impurities representing 10% or more of the material in the band. A method for detecting lower levels of impurities has been developed grounded upon the same general principle applied in the initial isolation method. The method requires that the desired nucleotide sequence fragment contain a recognition site for a restriction endonuclease not employed in the initial isolation. Treatment of polynucleotide material, eluted from a gel electrophoresis band, with a restriction endonuclease capable of acting internally upon the desired sequence will result in cleavage of the desired sequence into two sub-fragments, most probably of unequal length. These sub-fragments upon electrophoresis will form two discrete bands at positions corresponding to their respective lengths, the sum of which will equal the length of the polynucleotide prior to cleavage. Contaminants in the original band that are not susceptible to the restriction enzyme may be expected to migrate to the original position. Contaminants containing one or more recognition sites for the enzyme may be expected to yield two or more sub-fragments. Since the distribution of recognition sites is believed to be essentially random, the probability that a contaminant will also yield sub-fragments of the same size as those of the fragment of desired sequence is extremely low. The amount of material present in any band of radioactively labeled polynucleotide can be determined by quantitative measurement of the amount of radioactivity present in each band, or by any other appropriate method.

Following the foregoing separation or any other technique that isolates the desired gene, the sequence may be reconstituted. The enzyme DNA ligase, which catalyzes the end-to-end joining of DNA fragments, may be employed for this purpose. The gel electrophoresis bands representing the sub-fragments of the desired sequence may be separately eluted and combined in the presence of DNA ligase, under the appropriate conditions. Where the sequences to be joined are not blunt-ended, the ligase obtained from *E. coli* may be used, Modrich, P, and Lehman, I. R., *J. Biol. Chem.* (1970) 245:3626.

The efficiency of reconstituting the original sequence from sub-fragments produced by restriction endonuclease treatment will be greatly enhanced by the use of a method for preventing reconstitution in improper sequence. This unwanted result is prevented by treatment of the homogeneous length cDNA fragment of desired sequence with an agent, such as alkaline phasphatase, capable of removing the 5'-terminal phosphate groups on the cDNA prior to cleavage of the homogeneous cDNA with a restriction endonuclease.

The majority of cDNA transcripts, under the conditions described above, are derived from the mRNA region containing the 5'-end of the mRNA template by specifically priming on the same template with a fragment obtained by restriction endonuclease cleavage. In this way, the above-described method may be used to obtain not only fragments of specific nucleotide sequence related to a desired protein, but also the entire nucleotide sequence coding for the protein of interest. Double-stranded, chemically synthesized oligonucleotide linkers, containing the recognition sequence for a restriction endonuclease, may be attached to the ends of the isolated cDNA, to facilitate subsequent enzymatic removal of the gene portion from the vector DNA. The vector DNA is converted from a continuous loop to a linear form by treatment with an appropriate restriction endonuclease. The ends thereby formed are treated with alkaline phosphatase to remove 5-phosphate end groups so that the vector DNA may not reform a continuous loop in a DNA ligase reaction without first incorporating a segment of the apoaequorin DNA. The cDNA, with attached linker oligonucleotides, and the treated vector DNA are mixed together with a DNA ligase enzyme, to join the cDNA to the vector DNA, forming a continuous loop of recombinant vector DNA, having the cDNA incorporated therein.

Transformation, as is understood in the an and used herein, denotes the process whereby a microorganism incorporates extracellular DNA into its own genetic constitution. Plasmid DNA may be so incorporated under appropriate environmental conditions. The incorporated plasmid undergoes replication in the transformed cell, and the replicated copies are distributed to progeny cells when cell division occurs. As a result, a new cell line is established, containing the plasmid and carrying the genetic determinants thereof. Transformation by a plasmid in this manner, where the plasmid genes are maintained in the cell line by plasmid replication, occurs at high frequency when the transforming plasmid DNA is in closed loop form, and does not or rarely occurs if linear plasmid DNA is used. Once a recombinant vector has been made, transformation of a suitable microorganism is a straightforward process, and novel microorganism strains containing the apoaequorin gene may readily be isolated, using appropriate selection techniques, as understood in the art.

In summary, genetic information can be obtained from Aequorea jellyfish, convened into cDNA, inserted into a vector, used to transform a host microorganism, and expressed as apoaequorin in the following manner:

1. Isolate poly(A+) RNA from Aequorea jellyfish.
2. Synthesize in vitro single-stranded cDNA and then double-stranded cDNA using reverse transcriptase.
3. Digest the single-stranded region with S1 nuclease.
4. Size-fractionate the double-stranded cDNA by gel filtration.
5. Tail the cDNA using terminal transferase and dCTP.
6. Digest pBR322 with PstI and then tail the linear DNA with terminal transferase and dGTP.
7. Anneal the dC-tailed cDNA fragment and dG tailed pBR322.
8. Transform *E. coli* SK1592. Select for tetracycline resistant colonies.
9. Screen the transformants for ampicillin sensitivity. The $tet^R$ $amp^S$ colonies contain recombinant plasmids. Store them at −80° C.
10. Label an oligonucleotide mixed probe (using a sequence deduced from the determined amino acid sequence) with radioactivity.
11. Grow the members of the Aequorea cDNA library on nitocellulose filters. Lyse the colonies and fix the DNA to the filters.
12. Hybridize the $^{32}$P-labeled oligonucleotide mixture to the nitrocellulose filters. The $^{32}$P-probe will hybridize to plasmid DNA from those *E. coli* recombinants which contain the aequorin cDNA sequence.
13. Wash excess $^{32}$P-probe from the filters.
14. Expose X-ray film to the filters.
15. Prepare plasmid DNA from the recombinants identified in the Aequorea cDNA bank.
16. Hybridize the $^{32}$P-labeled oligonucleotide to the plasmid DNA (Southern blot) to confine the hybridization.
17. Demonstrate that these recombinants contain the aequorin DNA sequence by preparing extracts in EDTA-containing buffers, pH 7.2. Charge the expressed apoprotein by adding coelenterate luciferin and β-mercaptoethanol and incubating at 4° C. overnight. A flash of blue light is emitted upon the addition of $Ca^{2+}$ from samples that express functional aequorin apoprotein.

Although the sequence of steps set forth above, when used in combination with the knowledge of those skilled in the art of genetic engineering and the previously stated guidelines, will readily enable isolation of the desired gene and its use in recombinant DNA vectors now that sufficient information is provided to locate the gene, other methods which lead to the same result are also known and may be used in the preparation of recombinant DNA vectors of this invention.

Expression of apoaequorin can be enhanced by including multiple copies of the apoaequorin gene in a transformed host, by selecting a vector known to reproduce in the host, thereby producing large quantities of protein from exogenous inserted DNA (such as pUC8, ptac12, or pIN-III-ompA1, 2, or 3), or by any other known means of enhancing peptide expression.

In all cases, apoaequorin will be expressed when the DNA sequence is functionally inserted into the vector. By "functionally inserted" is meant in proper reading fame and orientation, as is well understood by those skilled in the art. Typically, an apoaequorin gene will be inserted downstream from a promoter and will be followed by a stop codon, although production as a hybrid protein followed by cleavage may be used, if desired.

In addition to the above general procedures which can be used for preparing recombinant DNA molecules and transformed unicellular organisms in accordance with the practices of this invention, other known techniques and modifications thereof can be used in carrying out the practice of the invention. Any known system for expression of isolated genes is suitable for use in the present invention. For example, viral expression systems and the bacculovirus expression system are specifically contemplated within the scope of the invention. In particular, techniques relating to genetic engineering have recently undergone explosive growth and development. Many recent U.S. patents disclose plasmids, genetically engineering microorganisms, and methods of conducting genetic engineering which can be used in the practice of the present invention. For example, U.S. Pat. No. 4,273,875 discloses a plasmid and a process of isolating the same. U.S. Pat. No. 4,304,863 discloses a process for producing bacteria by genetic engineering in which a hybrid plasmid is constructed and used to transform a bacterial host. U.S. Pat. No. 4,419,450 discloses a plasmid useful as a cloning vehicle in recombinant DNA work. U.S. Pat. No. 4,362,867 discloses recombinant cDNA construction methods and hybrid nucleotides produced thereby which are useful in cloning processes. U.S. Pat. No. 4,403,036 discloses genetic reagents for generating plasmids containing multiple copies of DNA segments. U.S. Pat. No. 4,363,877 discloses recombinant DNA transfer vectors. U.S. Pat. No. 4,356,270 discloses a recombinant DNA cloning vehicle and is a particularly useful disclosure for those with limited experience in the area of genetic engineering since it defines many of the terms used in genetic engineering and the basic processes used therein. U.S. Pat. No. 4,336,336 discloses a fused gene and a method of making the same. U.S. Pat. No. 4,319,629 discloses plasmid vectors and the production and use thereof. U.S. Pat. No. 4,332,901 discloses a cloning vector useful in recombinant DNA. Although some of these patents are directed to the production of a particular gene product that is not within the scope of the present invention, the procedures described therein can easily be modified to the practice of the invention described in this specification by those skilled in the art of genetic engineering. In addition, other expression systems known in the art, such as viral expression systems and bacculovirus expression system in insects, may be employed. Transferring the isolated apoaequorin cDNA to other expression vectors will produce constructs which improve the expression of the apoaequorin polypeptide in *E. coli* or express apoaequorin in other hosts.

All of these patents as well as all other patents and other publications cited in this disclosure are indicative of the level of skill of those skilled in the art to which this invention pertains and are all herein individually incorporated by reference.

The implications of the present invention are significant in that unlimited supplies of homogeneous apoaequorin will become available for use in the development of luminescent immunoassays or in any other type of assay utilizing aequorin as a marker. The modified apoaequorin of the present invention has utility as a tracer in a wide range of medical and diagnostic assay systems. Modified apoaequorin having increased bioluminescent activity can replace in existing diagnostic and assay systems the tracer currently employed. Such currently employed tracers include radioactive atoms or molecules and color-producing enzymes such as horse-radish peroxidase. The benefits of using the apoaequorin of the present invention are at least four-fold: modified apoaequorin is safer than radioactive-based assays, modified apoaequorin generally is more sensitive than traditional tracers, modified apoaequorin can be assayed quickly and easily, and large numbers of samples can be handled simultaneously-reducing overall handling and increasing efficiency. Any ligand-ligator binding pair that can be modified with the apoaequorin of the present invention without disrupting the ability of each to bind to the other can form the basis of an assay encompassed by the present invention.

A ligand is any selectively bindable material that is bound by a specific binding body (a ligator). Examples of ligands include antigens, haptens, lectins, carbohydrates, glycoproteins, substrates and other molecules well known in the art. Examples of ligators include antibodies, receptors, lectins, chelators, enzymes and other molecules well known in the art.

The modified apoaequorin of the present invention can be used in any standard assay. Examples of such assays include competitive assays wherein labeled and unlabeled ligands competitively bind to a ligator, noncompetitive assay where a ligand is captured by a ligator and either measured directly or "sandwiched" with a secondary ligator that is labeled. Still other types of assays include immunoassays, single-step homogeneous assays, multiple-step heterogeneous assays, and enzyme assays. These and other assays are known in the art and their use with the apoaequorin of the present invention will become obvious to one skilled in the art in light of the teachings disclosed herein.

The invention will be more readily understood by reference to the following specific examples which are included for purposes of illustration only and are not intended to limit the invention unless so stated.

EXAMPLE 1

Purification of Native Aequorin

Aequorin was purified according to the method of Blinks et al. (J. R. Blinks, P. H. Mattingly, B. R. Jewell, M. van Leeuwen, G. C. Hatter, and D. C. Allen, *Methods Enzymol.* (1978) 57:292–328) except that Sephadex G-75 (superfine)is used in the second gel filtration step. The purification of aequorin took place as follows:

1. Collection of Aequorea in Friday Harbor, Wash., and removal of circumoral tissue (photocytes).
2. Extraction of proteins from photocytes via hypotonic lysis in EDTA.
3. Ammonium sulfate fractionation of photocyte extract (0–75%).
4. Centrifugation of ammonium sulfate precipitate; storage at −70° C., during and after shipment from Friday Harbor, Wash.
5. Gel filtration on Sephadex G-50 (fine).
6. Ion exchange on QAE Sephadex with pH step and salt gradient elution.
7. Gel filtration on Sephadex G-75 (superfine).
8. Ion-exchange on DEAE-Sephadex with pH-step and salt gradient elution.
9. Lyophilization (in EDTA) of pure aequorin and storage at −80° C.

Steps 1–4 were performed at Friday Harbor. Except for collection and removal of circumoral tissue, all steps are done at 0–4° C. The final product from Step 4 was stored on dry ice in 250 ml centrifuge bottles. The material was shipped in this form.

The purification of aequorin and green fluorescent protein (GFP) was done in Athens, Ga. (Steps 5–9). All steps were performed at 0–4° C. Aequorin-containing fractions were stored at −80° C. between steps; aequorin seems to be stable to freezing and thawing irrespective of protein concentration.

Step 5: Gel filtration on Sephadex G-50 (fine). Column dimensions: 5.8 cm×97 cm; 2563 ml. The column was run in 10 mM EDTA, pH 5.5 at a flow rate of 75 ml/hour. The GFP and aequorin eluted together on this column. 65–75% of the aequorin activity was pooled for subsequent purification. Side fractions were also pooled and stored for later purification. Aequorin yield in this step varied from 50% to 80%; 65–75% yields were usually achieved. The capacity of the column was approximately 1000 mg in 75 ml; generally smaller volumes were loaded whenever possible.

Step 6: Ion-exchange on QAE Sephadex. Column dimensions: 5 cm diameter. Five grams of dry Sephadex were used in this step.

Generally the pooled material from 6 to 10 initial G-50 steps was run on this column. Overall yield was improved by doing this, as was efficiency. This step was performed exactly as described by Blinks et al. (1978). After the column was loaded, the GFP was selectively eluted with a pH-step (5 mM Na Ac, 5 mM EDTA, pH 4.75). Aequorin was then eluted in a linear NaCl gradient in 10 mM EDTA, pH 5.5 (500 ml total volume). The GFP was made 10 mM in Tris and the pH raised to 8.0 for storage at −80° until further purification. The aequorin pool was concentrated via ultrafiltration (Amicon YM-10 membrane) in preparation for the next step. Aequorin yield: 80%. Step 7: Gel filtration on Sephadex G-75 (superfine).Column dimensions: 2.8 cm×150 cm; 924 ml total volume. The column was run in 10 mM EDTA, pH 5.5 at 10 ml/hour. Aequorin yield: 60–80%. Step 8: Ion-exchange on DEAE-Sephadex. The pooled aequorin from step 7 was run directly onto this column, which was run exactly as the QAE Sephadex column. The aequorin yield was generally 75–80%. This step is unnecessary with most aequorin preps. The material from step 7 is usually pure, according to SDS-PAGE in 12% acrylamide. Step 9: Aequorin was lyophilized with >95% recovery provided that some EDTA was present. Recoveries varied from 0% to 95% in the absence of EDTA (see Blinks et al., 1978).

EXAMPLE 2

Sequencing Methodology Applied in the Sequence Determination of Aequorin

Amino acid sequence analysis was performed using automated Edman Degradation (Edman and Begg, 1967). The sequence analysis of relatively large amounts of protein or peptide (10 nmol or more)was carried out using a Model 890 B Beckman sequencer (Duke University) updated as described by Brown et al. (1980)and employing a 0.55M Quadrol program with polybrene (Tarr et al., 1978). Two peptides, M3 and MS, which were small or appeared to wash out of the cup with the Quadrol method, were sequenced using a program adapted for dimethylallylamine buffer and polybrene as suggested by Klapper et al. (1978).

Phenylthiohydantion (PTH-) derivatives of amino acids were identified using reverse phase HPLC chromatography on a DuPont Zorbay ODS column essentially as described by Hunkapiller and Hood (1978). Peptides which were available at the 2–10 nmol level were sequenced on a Model 890 C Beckman sequencer (University of Washington) using a program for use with 0.1M Quadrol (Brauer et al., 1975) and polybrene. PTH-amino acids were identified using the reverse phase HPLC system described by Ericsson et al. (1977). An applied Biosystems Model 470A gas phase sequencer (University of Washington) (Hunkapiller et al., 1983) was used for sequence analysis when there was less than 1.5 nmol of peptide available. PTH amino acids from the gas phase instrument were identified using an IBM Cyano column as described by Hunkapiller and Hood (1983).

References

Edman, P. and Begg, G., *Eur. J. Biochem.*, 1, 80–91 (1967).
Brown, A. G., Cornelius, T. U., Mole, J. E., Lynn, J. D., Tidwell, W. A., and Bennett, J. C., *Anal. Biochem.*, 102, 35–38 ( 1980 ).
Terr, G. E., Beechnet, J. F., Bell, M., and McKean, D. J., *Anal. Biochem.*, 84, 622–627 (1978).
Klapper, D. G., Wilde, C. E., III and Capra, J. D., *Anal. Biochem.*, 85, 1 26–1 31 (1978).
Hunkapiller, M. W., and Hood, L. E., *Biochemistry*, 17, 2124–2133 (1978).
Brauer, A. W., Margolies, M. N., and Haber, E., *Biochemistry*, 13, 3029–3035 (1975).
Ericsson, L. H.,Wade, R. 1)., Gagnon, J., McDonald, R. R. and Walsh, K. A. in *Solid Phase Methods in Protein Sequence Analysis* (Previero, A. and Coletti-Previero, M. A.,eds.) pP. 137–142, Elsevier/North Holland, Amsterdam (1977).
Hunkapiller, M. W., Hewick, R. M., Dreyer, W. J., and Hood, L. E., *Methods Enzymol.*, 91., 399–413 (1983).
Hunkapiller, M. W., and Hood, L. E., *Methods Enzymol.*, 91, 486–493 (1983).

EXAMPLE 3

Cloning and Expression of a cDNA Coding for Apoaequorin MATERIALS AND METHODS

Restriction enzymes were purchased from Bethesda Research Laboratories, New England Bio Labs and International Biotechnologies, Inc. and used according to conditions described by the supplier. RNasin and reverse transcriptase were obtained from Biotech and Life Sciences, respectively. Terminal transferase was purchased from PL Biochemicals-Coelenterate luciferin was synthesized as described [Hori, K., Anderson, J. M., Ward, W. W. and Cormier, M. J., *Biochemistry*, 14, 2371–2376 (1975); Hori, K., Charbonneau, H, Hart, R. C., and Cormier M. J., *Proc. Nat'l. Acad. Sci.*, USA, 74, 4285–4287 (1977); Inouye, S., Sugiura, H. Kakoi, H., Hasizuma, K., Goto, T., and Iio, H., *Chem. Lett.*, 141–144 ( 1975)] and stored as a lyophilized powder until needed.

RNA Isolation and In Vitro Translation

*Aequorea victoria* jellyfish were collected at the University of Washington Marine Biology Laboratory at Friday Harbor, Wash. The circumoral tings were cut from the circumference of the jellyfish and immediately frozen in a dry ice/methanol bath. The tissue was kept at −70° C. until needed.

RNA was isolated according to the method of Kim et al. [Kim, Y-J., Shuman, J., Sette, K., and Przybyla, A., *J. Cell. Biol.*, (1983) 96:393–400] and poly(A)$^+$RNA was prepared using a previously described technique [Aviv and Leder, PNAS 69 (1972) 1408–1412].

Poly(A)$^+$RNA (1 µg) and poly(A$^-$)RNA (20 µg) were translated using the rabbit reticulocyte in vitro translation system (Pelham and Jackson, *Eur. J. Biochem.* (1976) 247; W. C. Merrick in *Methods in Enz.* 101(c) (1983) 606–615). The lysate was stripped of its endogenous mRNA with micrococcal nuclease. Each translation (62 µl total volume) was incubated 90 min at 25° C. in the presence of $^{35}$S-methionine (38 µCi). Two µl of each translation were removed for analysis by electrophoresis. Apoaequorin was immunoprecipitated by adding anti-aequorin (2 µl) and *Staph. aureus* cells to 50 µl of each translation mixture. After several washings, the antibody—apoaequorin complex was dissociated by heating in the presence of SDS. The translated products were analyzed on a SDS polyacrylamide (13%)gel. Following electrophoresis the gel was stained with Coomassie 250 to identify the protein standards and then the gel was impregnated with PPO in DMSO. Fluorography was performed at −70° C.

Recombinant DNA Procedures

Double-stranded cDNA was synthesized from total Aequorea Poly(A)$^+$RNA as described by Wickens et al., (Wickens, M. P., Buell, G. N., and Schimke, R. T., *J. Biol. Chem.* (1978)253:2483–2495). After addition of homopolymeric dC tails, double-stranded cDNA was annealed to dG-tailed PstI-digested pBR322 (Villa-Komaroff, L., Efstradiadis, A., Broome, S., Lomedico, P., Tizard, R., Naber, S. P., Chick, W. L., and Gilbert, *PNAS* (1978) and used to transform *E. coli* strain SK1592. Tetracycline-resistant, ampicillin-sensitive colonies were transferred to and frozen in microliter dishes at −70° C.

The Aequorea cDNA library was screened for the aequorin cDNA using a synthetic oligonucleotide mixture. The oligonucleotide mixture (17-mers) was supplied by Charles Cantor and Carlos Argarana (Columbia University). Following their purification by polyacrylamide electrophoresis [Maniatis, T., and Efstratidis, A., *Meth. in Enz.* (1980) 65:299–305] and the oligonucleotides were radioactively labelled using polynucleotide kinase and gamma −$^{32}$P-ATP [Maxam, A. M. and Gilbert, W., *Meth. in Enz.* (1980). The unincorporated $^{32}$P was removed by DEAE-cellulose ion exchange chromatography.

The Aequorea cDNA library was screened in the following manner: The *E. coli* recombinants were transferred from frozen cultures to nitrocellulose filters (7×11 cm) placed on Luria agar plates. The colonies were grown 12 hours at 37° C. and lysed and then the DNA was fixed as Taub and Thompson *Anal. Blochem.* (1982) 126:222–230] described for using Whatman 541 paper. The filters were baked under vacuum for 2 hours after they had been air-dried.

The filters were incubated at 55° C. for 12–20 hours in 3 ml/filter of a prehybridization solution (10× NET, 0.1% SDS, 3× Denhardt's) after first wetting them in 1×SSC. The solution was poured from the hybridization bag and replaced with 1 ml/filter of the hybridization solution (10×NET, 0.1% SDS, 3× Denhardt's, 1×10$^6$ cpm $^{32}$P-labelled 17-mers per filter). The hybridization was carried out for 24 hours at 37° C. after which the filters were washed four times in 10×SSC at 4° C. for 10 min. The filters were air dried and then wrapped in plastic wrap. Kodak XAR5 film was exposed to the filters at −70° C. using a DuPont Cronex intensifying screen.

Growth and Extraction Procedures for *E. coli*

*E. coli* SK1592 containing pAEQ1 - pAEQ6 were grown overnight in 25 ml of Luria broth at 37° C. The cells were centrifuged and then resuspended in 5 ml of 10% sucrose, 50 mM Tris pH 8. The cells were lysed with the addition of the following: 7.2 µl of 0.1M phenylmethylsulfonylfluoride, 312 µl of 0.2M EDTA, 10 mg lysozyme, and 10 µl of 10 mg/ml RNase A. After 45 min on ice, the mixture was centrifuged at 43,500×g for one hour. The supernatant was saved.

Purification and Assay of Aequorin

Aequorin was extracted and purified by the method of Blinks et al, [Blinks, J. R., Wier, W. G., Hess, P., and Prendergast, F. G., *Prog. Biophys. Molec. Biol* (1982) 40:1–114]. Aequorin, or photoprotein activity, was measured by injecting 5 µl of the sample into 0.5 ml of 0.1M CaCl$_2$, 0.1Tris, pH 8.0 and simultaneously measuring peak light intensity and total photons. The design of photometers for making such measurements and calibrating the instrument for absolute photon yields have been previously described [Anderson, J. M, Faini, G. J., and Wampler, J. E., *Methods in Enz.* (1978) 57:529–559; Charbonneau, H., and Cormier, M. J., *J. Biol. Chem.* (1979) 254:769–780].

Partial Purification of Apoaequorin Activity in SK1592/pAEQ1 Extracts

The expressed apoaequorin was partially purified by passage of 23 ml of a SK1592/pAEQ1 extract over a 42 ml bed volume of Whatman DE-22 equilibrated in 1 mM EDTA, 1.5 mM Tris, pH 7.5. An 800 ml NaCl gradient (0–1M) was applied and the active apoaequorin eluted at 0.3M NaCl. The peak fractions were pooled and dialyzed against 0.5M KCl, 10 mM EDTA, and 15 mM Tris, pit 7.5 for the experiments described in FIG. 3.

In Vitro Translation of Aequorea poly(A+)RNA

Approximately 1.6 µg poly(A+)RNA was isolated from each gram of frozen jellyfish tissue. The results of the in vitro translation of the Aequorea poly(A$^+$)RNA in the presence of $^{35}$S-Met are shown in FIG. 1. The translation products which reacted with anti-aequorin are shown in lane 4. The $^{35}$S radioactivity immunoprecipitated represented 0.3% of the total acid-precipitable counts in the translation implying that the apoaequorin mRNA represents approximately 0.3% of the total poly(A$^+$) mRNA. This relative abundance agrees well with the fraction of total protein (0.5%) which corresponds to aequorin in a crude extract of circumoral tings from Aequorea. No proteins were immunoprecipitated when the in vitro translation was performed in the absence of Aequorea RNA (lane 2) or in the presence of Aequorea poly(A−)RNA (data not shown).

Figure 4:
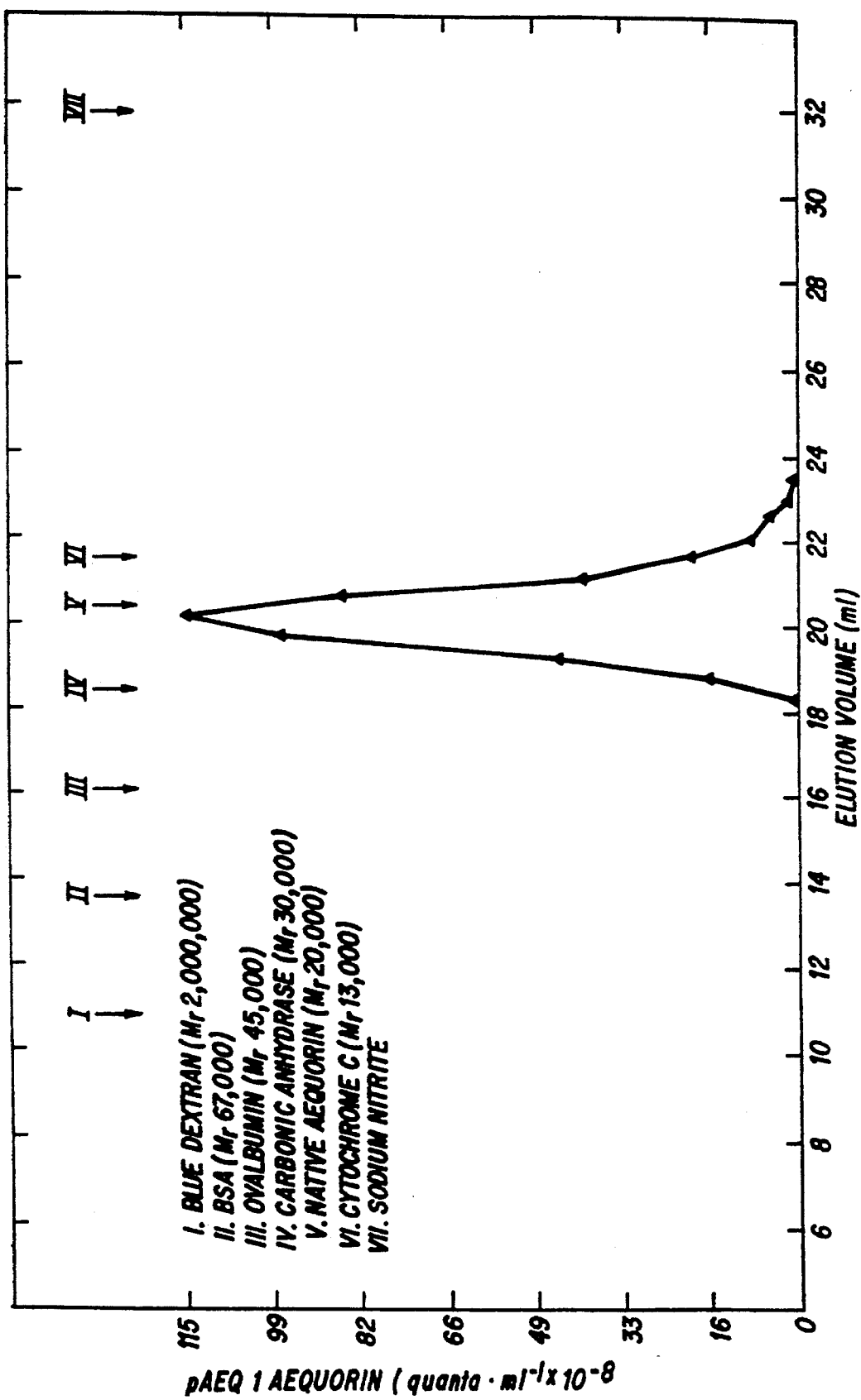
FIG. 4 is a graph of a gel filtration profile of the $Ca^{2+}$-dependent photoprotein activity generated from pAEQ1 extracts. Partially purified apoaequorin activity from pAEQ1 extracts were used to generate $Ca^{2+}$-dependent photoprotein activity as described in FIG. 3. This photoprotein fraction (50 μl) was then placed on a G-75-40 superfine column (30.7 ml bed volume) equilibrated with 10 mM EDTA, 15 mM Tris, pH 7.5 and 100 mM KCL. The elution positions of various molecular weight markers are indicated.

The primary translation products immunoprecipitated with the anti-aequorin migrated on the SDS-PAGE gel with an apparent molecular weight (23,400 daltons, lane 4) slightly greater than that for native aequorin isolated from Aequorea (22,800 daltons, indicated in FIG. 1). This data, and the data shown in FIG. 4, are consistent with the presence of having an additional seven amino acids than in native aequorin.

The proteins immunoprecipitated from the poly(A⁺)RNA translation migrated as a doublet or even a triplet (lane 4, FIG. 1) if one studies the original autoradiogram. This result can be interpreted in two ways. First, multiple apoaequorin genes may exist in *Aequorea victoria* and code for proteins that differ in molecular weight due to various lengths of their amino acid sequences. Aequorin isozymes [Blinks, J. R., and Hatter, G. C., *Fed. Proc.* (1975) 34:474] may be indicative of such a multi-gene family. Second, the *Aequorea victoria* population at Friday Harbor may consist of several species of Aequorea.

The Aequorea cDNA library used contained 6000 recombinants having inserts greater than 450 bp. Of 25 random recombinants screened, none had inserts less than 500 bp and two were larger than 3 kb.

The Aequorea cDNA library was screened with the following mixed synthetic oligonucleotide probe:

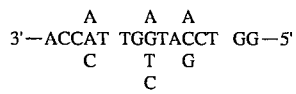

Figure 2:
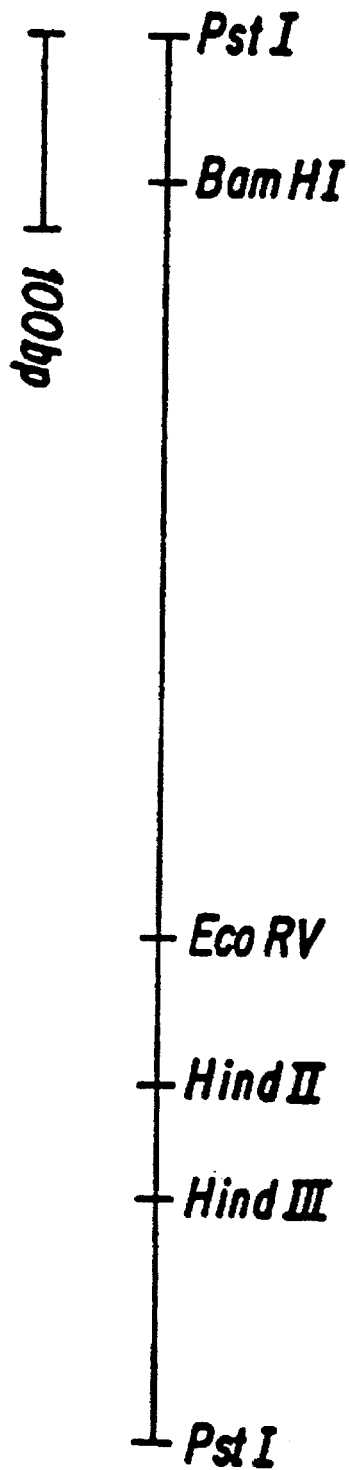
FIG. 2 is a restriction map of a gene isolated from an *Aequeous victoria* jellyfish that contains a DNA sequence coding for apoaequorin.

The DNA sequences of these oligonucleotides were determined by an examination of the complete amino acid sequence of apoaequorin. These oligonucleotides are complementary to the mRNA which codes for the peptide Trp¹⁶⁶. Tyr. Thr. Met. Asp. pro¹⁷¹ in the carboxy terminus-region of the aequorin polypeptide. The 17-mers were ³²P-labelled and hybridized to plasmid DNA from the Aequorea cDNA library as described in Methods. Six transformants were identified which contained plasmids having inserts that hybridized to the synthetic oligonucleotides. The restriction map of the plasmid containing the largest PstI insert, pAEQ1, is shown in FIG. 2. No hybridization of the synthetic oligonucleotides would occur if pAEQ1 was digested with BamHI, whose recognition sequence (GGATCC) is contained within four of the 17-mers. Hence, the BamHI, site in pAEQ 1 could be used to identify the 3'-region of the apoaequorin coding sequence. The recombinant plasmid pAEQ1 does indeed contain the apoaequorin cDNA as demonstrated by its expression in *E. coli*, as described below.

Expression of Apoaequorin in *E. coli*

In order to find out whether any of these six transformants were producing biologically active apoaequorin, extracts of each plus the host strain, were prepared as described in Methods. To 0.5 ml of each extract was added β-mercaptoethanol (2 mM) and coelenterate luciferin (0.1 mM) and the mixture allowed to incubate at 4° C. for 20 hours. This mixture was then assayed for Ca²⁺-dependent photoprotein activity as described in above. Ca²⁺-dependent luminescence was observed in extracts prepared from the recombinant strain containing pAEQ1, but no such luminescence was observed in extracts of the host strain or in extracts derived from any of the other transformants. The inserts in the plasmids DNA sequences. However, if the cDNA inserts in pAEQ2–6 were not of sufficient length or oriented improperly within the plasmid, apoaequorin activity in those extracts would not be expected.

Figure 3:
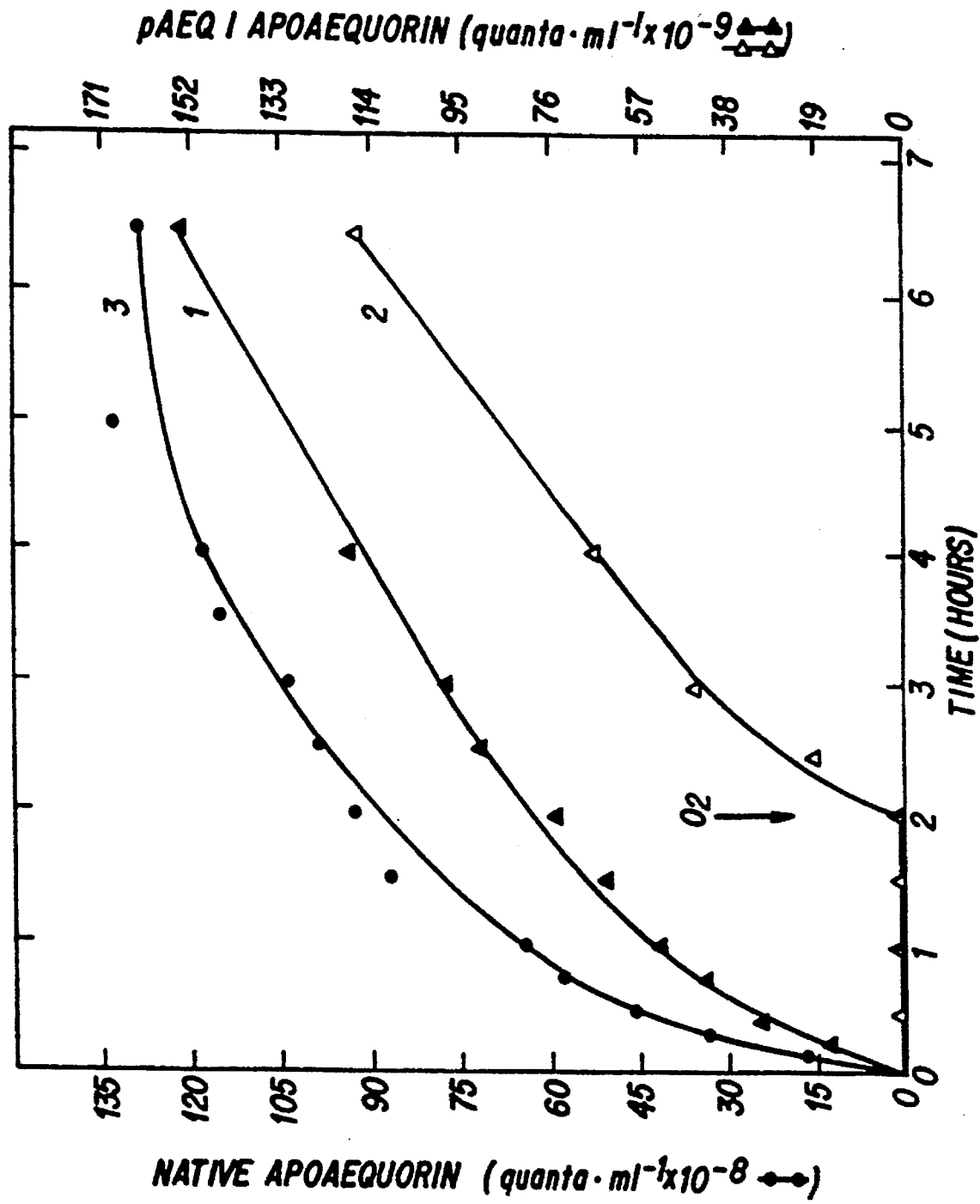
FIG. 3 is a graph of time- and oxygen dependent formulation of $Ca^{2+}$-dependent photoproteinactivity in pAEQ1 extracts. Conditions used: (a) In curves 1 and 2, 0.5 ml aliquots of the active fractions were made 2 mM in B-mercaptoethanol and 0.1 mM in coelenterate luciferin and incubated at 4 for the times indicated. At appropriate time intervals, 5 μl aliquots were removed and assayed for photoprotein activity. (b) In curve 2, dissolved $O_2$ levels were reduced by bubbling with Ar gas and the mixture exposed to oxygen at the time indicated (c)In curve 3, native apoaequorin was used in the incubation mixture in place of the pAEQ1 extract.

The kinetics of formation of photoprotein activity from extracts of SK1592/pAEQ1 is similar to that observed with native apoaequorin as shown in FIG. 3. Requirements for the formation of photoprotein activity in this extract is also identical to that observed when authentic apoaequorin, prepared from native aequorin, is used. As FIG. 3 shows, dissolved $O_2$ is required. Furthermore, the elimination of either β-mercaptoethanol or coelenterate luciferin from the reaction mixture results in zero production of Ca²⁺-dependent photoprotein activity. Injection of the active component into Ca²⁺- free buffers produced no luminescence. The subsequent addition of Ca²⁺ resulted in a luminescence flash.

To further characterize the active component, the extracts of SK1592/pAEQ1 was subjected to chromatography over DE-22 as described in Methods. The apoaequorin activity eluted at about 0.3M salt which is similar to that observed for authentic apoaequorin. The active fractions were then incubated in the presence of coelenterate luciferin, β-mercaptoethanol and oxygen to generate photoprotein activity as described in FIG. 3. This mixture was then subjected to gel filtration. As FIG. 4 shows, the photoprotein activity generated from the partially purified component in SK1592/pAEQ1 extracts eluted from the column with an $M_r$ of 20,600 as compared to a value of 19,600 for native aequorin. Similar results were observed during in vitro translation experiments (FIG. 1). From the data of FIG. 4, one may also conclude that the luciferin becomes tightly associated with the active component in SK1592/pAEQ1 extracts under the charging conditions used.

The pooled photoprotein fraction from FIG. 4 produces a luminescence flash upon the addition of Ca²⁺. The kinetics of this flash was indistinguishable from the kinetics of the Ca²⁺-dependent aequorin reaction. Other recombinant plasmids did not express a light-emitting protein when present in transformants, as is shown in Table 3 below.

The above data suggest that the cDNA inserted into pAEQ1 represents the full-length cDNA coding for apoaequorin. The data also show that the Ca²⁺-dependent photoprotein activity is expressed in SK1592/pAEQ1 and that the protein product is indistinguishable in its biological properties from that of changed native apoaequorin. The level of expression was estimated to be about 0.01% of the total soluble protein.

TABLE 3

| Recharging of *E. coli* Extracts Containing Apoaequorin cDNAs | | |
|---|---|---|
| cDNA | Peak Light Intensity (hv/sec-1) in Extracts +Ca²⁺ | –Ca²⁺ |
| pAEQ1 | 5 × 10⁶ | 0 |
| pAEQ2 | 0 | 0 |
| pAEQ3 | 0 | 0 |
| pAEQ4 | 0 | 0 |
| pAEQ5 | 0 | 0 |
| pAEQ6 | 0 | 0 |
| SK1592 (Host Strain) | 0 | 0 |

To 0.5 ml of each extract was added mercaptoethanol (2 μM) and coelenterate luciferin (0.1 ram). The mixture was incubated at 4° C. for 20 hours. A 5 μl sample was removed, injected into 0.5 ml of 0.1 mM CaCl₂ and peak light intensity measured.

In addition to the above described examples of the isolation, sequencing, and expression in a microorganism of recombinant apoaequorin, altered forms of apoaequorin may be produced having increased bioluminescent activity relative to naturally occurring or unmodified recombinant apoaequorin. The sequences of modified apoaequorin the present invention are distinct from those of Tsuji et al., discussed above, because the present invention (1) encompasses different amino acid substitutions, and more importantly, (2) relates solely to modified apoaequorins having increased bioluminescent light emitting activity relative to naturally occurring or recombinant unmodified aequorin. Further, the modified sequences of the present invention are not rendered obvious in light of Tsuji et al., because Tsuji et al. teaches away from modified aequorins having increased bioluminescent activity. As illustrated in Table 2 of Tsuji et al., every amino acid replacement resulted in lowered bioluminescent activity in fully regenerated aequorin. Tsuji teaches that amino acid replacement in a $Ca^{2+}$-binding site is expected to result in lowered activity. In fact, Tsuji, et al. reports that amino acid replacement G3R, substituting arginine for glycine at amino acid position 158, unexpectedly resulted in almost normal activity levels. An increase in bioluminescent activity as a result of an amino acid substitution, as encompassed by the present invention is, therefore, even more unexpected. The modified apoaequorin sequences of the present invention are illustrated by the following non-limiting examples.

EXAMPLE 4

DESCRIPTION OF THE MUTAGENESIS PROCEDURE

The method described by Lewis and Thompson (Nuc. Acid Res. 18(12):3439, 1990), herein incorporated by reference, was utilized to create a variety of modified aequorin proteins having increased bioluminescent activity relative to unmodified apoaequorin. The mutagenesis system, purchased commercially from Promega Corp. (Madison, Wis.), consists of a unique mutagenesis vector and a simple antibiotic resistance selection of oligonucleotide-directed mutants. The system uses a phagemid vector, pSELECT-1, which contains two genes for antibiotic resistance, one towards tetracycline and the other towards ampicillin. However, the gene encoding the ampicillin resistance has been inactivated. The repair of this gene during the mutagenesis reaction provides a selection for the presence of the mutant strand, thus yielding a high percentage of mutants.

Specifically, the 531 bp HindIII/BamH1 aequorin fragment, which encodes amino acids number 9 through 185 of the 196 amino acid aequorin sequence, was subcloned into HindIII+BamIII-digested pSELECT-1 phagemid vector provided in the mutagenesis kit. The resulting aequorin-containing pSELECT derivative was named pAEQ3.6. Single-stranded DNA was prepared from this derivative with the aid of a helper phage (either M13K07 or R408) provided in the mutagenesis kit. Next, two oligonucleotides were annealed to the DNA during each mutagenesis reaction. The first oligonucleotide, a mutagenic oligonucleotide produced by methods well known to those skilled in the art, was designed to alter the aequorin sequence at a single amino acid (or in the case of pAEQ3.32 and pAEQ3.34 at two amino acids). The second oligonucleotide annealed to the single stranded DNA is part of the mutagenesis kit and is designed to repair the inactivated ampicillin gene restoring ampicillin resistance. The annealed complex was made double-stranded with DNA polymerase and any nicks were sealed with DNA ligase.

This DNA was then transformed into a repair minus strain of E. coli (BMH 71–18) to suppress in vivo mismatch repair, and grown overnight in the presence of ampicillin. A second round of transformation (into E. coli JM 109) ensured proper segregation of mutant and wild type plasmids and generally resulted in a high proportion of mutants. Cells from the second transformation were then selected on ampicillin-containing agar plates. Individual colonies were then analyzed by DNA sequencing for the presence of a recombinant plasmid containing the pSELECT derivative having the altered aequorin sequence of interest.

An expression vector was constructed using the mutagenized HindIII/BamH1 fragment isolated from the new pSELECT derivative. A preparation of plasmid DNA containing the entire aequorin nucleotide coding sequence had been previously digested with the same restriction enzymes for the purpose of removing the 531 bp HindIII/BamH1 fragment of the wild-type aequorin sequence. The 5' and 3' portions of the wild-type coding sequence were still contained in the vector fragment. Ligation of the mutagenized 531 bp fragment into this 'vector preparation' regenerated the aequorin coding sequence with the altered nucleotides as defined in the mutagenic oligonucleotide substituting for the wild-type 531 bp fragment. Several E. coli recombinants, transformed with this ligation product, were then analyzed by DNA sequencing for the presence of the expression vector containing the entire aequorin coding sequence with the intended modifications. Only following this verification was the strain used to produce recombinant apoaequorin protein.

DESCRIPTION OF THE BACTERIAL EXPRESSION SYSTEM.

The plasmid used to create all of the aequorin expression vectors is a derivative of pRC23 originally described by Crowl, et. al. (Gene 38:31–38, 1985), herein incorporated by reference. This plasmid contains the lambda $P_L$ promoter which drives transcription across the inserted cDNA, aequorin in this case. Ampicillin resistance is also encoded on the plasmid. The $P_L$ promoter is regulated by the presence of a temperature-sensitive cI gene product present within the same E. coli cell. The cI protein is encoded on a second plasmid pRK248ts as described by Bernard and Helinski (Meth. in Enzymol. 68:482–492, 1979), herein incorporated by reference, which also encodes tetracycline resistance. When an E. coli strain containing both plasmids is grown at 30° C., the cI protein is active and represses transcription at the $P_L$ promoter. Following a thermal shock at 42° C. the cI protein is inactivated permitting transcription of the cDNA inserted 3' to the $P_L$ promoter.

A variety of expression vectors have been constructed containing coding sequences that have been altered using site-directed mutagenesis. Each mutant has replaced either one or two amino acids whose putative role is to serve as ligand residues for the binding of $Ca^{2+}$ (or other certain divalent cations). These replacements were incorporated to test the role of each of the three $Ca^{2+}$ binding sites in the luminescent activity. Measurements of total light yield (photons per mg protein at saturating $Ca^{2+}$) of six of these modified aequorins produced surprising results (Table 4). Three modified aequorins having amino acid replacements in binding site 1 showed reduced activity as expected. However, three modified aequorins having amino acid replacements in binding site 2 showed enhanced activity when compared to unaltered aequorin with the wild-type amino acid sequence (Table 4). More specifically, the modified aequorins are up to approximately 2.5 times more active than unmodified recombinant aequorin. Additionally, other expression vectors have been constructed that produce modified aequorins having still other amino acid replacements, but the modified recombinant aequorins produced by these expression vectors have not yet been characterized.

TABLE 4

Site-Directed Mutants of Apoaequorin

| Amino Acid Replacement | Ca Site Modified | Expression Vector Number | % Relative Activity (saturating Calcium) |
|---|---|---|---|
| WF | all normal | pAEQ3.2 | 100% |
| D31S | 1 | pAEQ3.13 | 44% |
| E42S | 1 | pAEQ3.12 | 94% |
| G36A | 1 | pAEQ3.14 | 73% |
| E42S/D31S | 1 | pAEQ3.32 | NA |
| D124S | 2 | pAEQ3.20 | 231% |
| E135S | 2 | pAEQ3.22 | 124% |
| G129A | 2 | pAEQ3.15 | 142% |
| D124S/E135S | 2 | pAEQ3.34 | NA |
| G129R | 2 | pAEQ3.28 | NA |
| D160S | 3 | pAEQ3.18 | NA |
| E171S | 3 | pAEQ3.24 | NA |
| G165A | 3 | pAEQ3.16 | NA |

NA = Not Available; WT specific activity = approximately $1 \times 10^{16}$ photons/mg protein;
D = aspartic acid, S = serine, E = glutamic acid, G = glycine, A = alanine and R = arginine, WT = wild-type.

The amino acid sequences of the modified recombinant apoaequorins having bioluminescent activity greater than unmodified apoaequorin are shown below as SEQ ID NO: 3, SEQ ID NO: 4, and SEQ ID NO: 5.

It is clear from the work of Tsuji, et al., and from the first 3 mutations indicated above in Table 4, that most changes in amino acids in putative apoaequorin calcium binding sites result in reduced bioluminescent activity. The dramatic increase in bioluminescent activity resulting from some of the amino acid substitutions of the present invention was wholly unexpected.

EXAMPLE 8

Immunoassay using Modified Apoaequorin

A molecule, e.g. an antigen, may be detected in the following manner. First, antibodies specific for the antigen are made by standard methods well known in the art. The antibodies can be either polyclonal or monoclonal. These antibodies are immobilized to a solid surface such as the well of a microtiter plate and serve to "capture" and immobilize the antigen from the sample to be assayed. Such samples may be blood, urine or other body fluids. Additionally, the sample could be reaction mixture of a production process or an aliquot from a purification protocol. Upon mixing of the sample and the immobilized antibody, antigen contained in the sample will be specifically bound. The remainder of the sample is then removed by washing the microtiter well. Generally a second antibody, either monoclonal or polyclonal, that is labeled with antigen-first antibody complex as a tracer is next added to the microtiter well and allowed to bind to the antigen-first antibody complex, thus forming a sandwich. Excess second antibody is washed out of the microliter well and the presence of antigen determined by assaying for the emission of light upon the addition of light-triggering cation such as $Ca^{2+}$, as described above.

Alternatively, the second antibody can be unlabeled in which case the second antibody is itself in turn bound by an antibody or other ligator, such as goat-anti-rabbit IgG where the second antibody is raised in rabbits. In such a case, the goat-anti-rabbit IgG specific for the second antibody is labeled with modified apoaequorin. Light emission in the presence of luciferin and a light-triggering cation such as $Ca^{2+}$ is measured as described above.

The invention now being fully described will be apparent to one of ordinary skill in the art and that many changes and modifications can be made thereto without departing from the spirit or scope of the invention as set forth herein.

SEQUENCE LISTING ( 1 ) GENERAL INFORMATION:

( i i i ) NUMBER OF SEQUENCES: 10

( 2 ) INFORMATION FOR SEQ ID NO: 1:

( i ) SEQUENCE CHARACTERISTICS:
        ( A ) LENGTH: 196 amino acids
        ( B ) TYPE: amino acid
        ( D ) TOPOLOGY: linear ( i i ) MOLECULE TYPE: protein ( i x ) FEATURE:
        ( A ) NAME/KEY: Recombinant Aequorin
        ( D ) OTHER INFORMATION: Bioluminescent protein ( x ) PUBLICATION INFORMATION:
        ( A ) AUTHORS: Prasher et al.
        ( B ) TITLE: Sequence Comparisons of Complementary DNAs Encoding Aequorin Isotypes
        ( C ) JOURNAL: Biochemistry
        ( D ) VOLUME: 26
        ( F ) PAGES: 1326-1332
        ( G ) DATE: 1987

( K ) RELEVANT RESIDUES IN SEQ ID NO: 1: Points of
microheterogeneity where specific amino acid
replacements may occur and still retain bioluminescent
activity in the protein are residues: 4, 12, 15, 18, 37
70, 71 85 88, 95, 98, 99, 102, 103, 105, 108, 109, 114,
123, 132, 142, 148, 157, and 164.

( x i ) SEQUENCE DESCRIPTION: SEQ ID NO: 1:

| Met | Thr | Ser | Glu | Gln | Tyr | Ser | Val | Lys | Leu | Thr | Pro |
|---|---|---|---|---|---|---|---|---|---|---|---|
| 1 | | | | 5 | | | | | 10 | | |

| Asp | Phe | Asp | Asn | Pro | Lys | Trp | Ile | Gly | Arg | His | Lys |
|---|---|---|---|---|---|---|---|---|---|---|---|
| | | 15 | | | | | 20 | | | | |

| His | Met | Phe | Asn | Phe | Leu | Asp | Val | Asn | His | Asn | Gly |
|---|---|---|---|---|---|---|---|---|---|---|---|
| 25 | | | | | 30 | | | | | 35 | |

| Arg | Ile | Ser | Leu | Asp | Glu | Met | Val | Tyr | Lys | Ala | Ser |
|---|---|---|---|---|---|---|---|---|---|---|---|
| | | | 40 | | | | | 45 | | | |

| Asp | Ile | Val | Ile | Asn | Asn | Leu | Gly | Ala | Thr | Pro | Glu |
|---|---|---|---|---|---|---|---|---|---|---|---|
| | 50 | | | | | 55 | | | | | 60 |

| Gln | Ala | Lys | Arg | His | Lys | Asp | Ala | Val | Glu | Ala | Phe |
|---|---|---|---|---|---|---|---|---|---|---|---|
| | | | | 65 | | | | | 70 | | |

| Phe | Gly | Gly | Ala | Gly | Met | Lys | Tyr | Gly | Val | Glu | Thr |
|---|---|---|---|---|---|---|---|---|---|---|---|
| | | 75 | | | | | 80 | | | | |

| Glu | Trp | Pro | Glu | Tyr | Ile | Glu | Gly | Trp | Lys | Arg | Leu |
|---|---|---|---|---|---|---|---|---|---|---|---|
| 85 | | | | | 90 | | | | | 95 | |

| Ala | Ser | Glu | Glu | Leu | Lys | Arg | Tyr | Ser | Lys | Asn | Gln |
|---|---|---|---|---|---|---|---|---|---|---|---|
| | | | 100 | | | | | 105 | | | |

| Ile | Thr | Leu | Ile | Arg | Leu | Trp | Gly | Asp | Ala | Leu | Phe |
|---|---|---|---|---|---|---|---|---|---|---|---|
| | 110 | | | | | 115 | | | | | 120 |

| Asp | Ile | Ile | Asp | Lys | Asp | Gln | Asn | Gly | Ala | Ile | Ser |
|---|---|---|---|---|---|---|---|---|---|---|---|
| | | | | 125 | | | | | 130 | | |

| Leu | Asp | Glu | Trp | Lys | Ala | Tyr | Thr | Lys | Ser | Ala | Gly |
|---|---|---|---|---|---|---|---|---|---|---|---|
| | | 135 | | | | | 140 | | | | |

| Ile | Ile | Gln | Ser | Ser | Glu | Asp | Cys | Glu | Glu | Thr | Phe |
|---|---|---|---|---|---|---|---|---|---|---|---|
| 145 | | | | | 150 | | | | | 155 | |

| Arg | Val | Cys | Asp | Ile | Asp | Glu | Ser | Gly | Gln | Leu | Asp |
|---|---|---|---|---|---|---|---|---|---|---|---|
| | | | 160 | | | | | 165 | | | |

| Val | Asp | Glu | Met | Thr | Arg | Gln | His | Leu | Gly | Phe | Trp |
|---|---|---|---|---|---|---|---|---|---|---|---|
| | 170 | | | | | 175 | | | | | 180 |

| Tyr | Thr | Met | Asp | Pro | Ala | Cys | Glu | Lys | Leu | Tyr | Gly |
|---|---|---|---|---|---|---|---|---|---|---|---|
| | | | | 185 | | | | | 190 | | |

| Gly | Ala | Val | Pro |
|---|---|---|---|
| | | | 195 |

( 2 ) INFORMATION FOR SEQ ID NO: 2:

( i ) SEQUENCE CHARACTERISTICS:
        ( A ) LENGTH: 189 amino acids
        ( B ) TYPE: amino acid
        ( D ) TOPOLOGY: linear ( i i ) MOLECULE TYPE: protein ( i x ) FEATURE:
        ( A ) NAME/KEY: Recombinant Aequorin
        ( D ) OTHER INFORMATION: Bioluminescent protein ( x ) PUBLICATION INFORMATION:
        ( A ) AUTHORS: Charbonneau et al.
        ( B ) TITLE: Amino acid sequence of the calcium-dependent
            photoprotein aequorin
        ( C ) JOURNAL: Am. Chem. Soc.
        ( D ) VOLUME: 24

(E) ISSUE: 24
(F) PAGES: 6762-6771
(G) DATE: 1985
(K) RELEVANT RESIDUES IN SEQ ID NO: 2: Points of
microheterogeneity where specific amino acid
replacements may occur and still retain bioluminescent
activity in the protein are residues: 12, 15, 18, 37,
70, 71, 85, 88, 95, 98, 99, 102, 103, 105, 108, 109,
114, 123, 132, 142, 148, 157, and 164.

(xi) SEQUENCE DESCRIPTION: SEQ ID NO: 2:

| Val | Lys | Leu | Thr | Pro | Asp | Phe | Asp | Asn | Pro | Lys | Trp |
| 1 | | | | 5 | | | | | 10 | | |
| Ile | Gly | Arg | His | Lys | His | Met | Phe | Asn | Phe | Leu | Asp |
| | | 15 | | | | | 20 | | | | |
| Val | Asn | His | Asn | Gly | Arg | Ile | Ser | Leu | Asp | Glu | Met |
| 25 | | | | | 30 | | | | | 35 | |
| Val | Tyr | Lys | Ala | Ser | Asp | Ile | Val | Ile | Asn | Asn | Leu |
| | | | 40 | | | | | 45 | | | |
| Gly | Ala | Thr | Pro | Glu | Gln | Ala | Lys | Arg | His | Lys | Asp |
| | 50 | | | | | 55 | | | | | 60 |
| Ala | Val | Glu | Ala | Phe | Phe | Gly | Gly | Ala | Gly | Met | Lys |
| | | | | 65 | | | | | 70 | | |
| Tyr | Gly | Val | Glu | Thr | Glu | Trp | Pro | Glu | Tyr | Ile | Glu |
| | | 75 | | | | | 80 | | | | |
| Gly | Trp | Lys | Arg | Leu | Ala | Ser | Glu | Glu | Leu | Lys | Arg |
| 85 | | | | | 90 | | | | | 95 | |
| Tyr | Ser | Lys | Asn | Gln | Ile | Thr | Leu | Ile | Arg | Leu | Trp |
| | | | 100 | | | | | 105 | | | |
| Gly | Asp | Ala | Leu | Phe | Asp | Ile | Ile | Asp | Lys | Asp | Gln |
| | 110 | | | | 115 | | | | | | 120 |
| Asn | Gly | Ala | Ile | Ser | Leu | Asp | Glu | Trp | Lys | Ala | Tyr |
| | | | | 125 | | | | | 130 | | |
| Thr | Lys | Ser | Ala | Gly | Ile | Ile | Gln | Ser | Ser | Glu | Asp |
| | | 135 | | | | | 140 | | | | |
| Cys | Glu | Glu | Thr | Phe | Arg | Val | Cys | Asp | Ile | Asp | Glu |
| 145 | | | | | 150 | | | | | 155 | |
| Ser | Gly | Gln | Leu | Asp | Val | Asp | Glu | Met | Thr | Arg | Gln |
| | | | 160 | | | | | 165 | | | |
| His | Leu | Gly | Phe | Trp | Tyr | Thr | Met | Asp | Pro | Ala | Cys |
| | 170 | | | | | 175 | | | | | 180 |
| Glu | Lys | Leu | Tyr | Gly | Gly | Ala | Val | Pro | | | |
| | | | | 185 | | | | | | | |

(2) INFORMATION FOR SEQ ID NO: 3:

(i) SEQUENCE CHARACTERISTICS:
(A) LENGTH: 196 amino acids
(B) TYPE: amino acid
(D) TOPOLOGY: linear (ii) MOLECULE TYPE: protein (ix) FEATURE:
(A) NAME/KEY: Recombinant site-directed aequorin mutant
(D) OTHER INFORMATION: Site-directed mutant having increased
bioluminescent activity.

(x) PUBLICATION INFORMATION:
(K) RELEVANT RESIDUES IN SEQ ID NO: 3: Asp 124 changed to Ser (xi) SEQUENCE DESCRIPTION: SEQ ID NO: 3:

| Met | Thr | Ser | Glu | Gln | Tyr | Ser | Val | Lys | Leu | Thr | Pro |
| 1 | | | | 5 | | | | | 10 | | |

| Asp | Phe | Asp | Asn | Pro | Lys | Trp | Ile | Gly | Arg | His | Lys |
| | | 15 | | | | | 20 | | | | |

| His | Met | Phe | Asn | Phe | Leu | Asp | Val | Asn | His | Asn | Gly |
| 25 | | | | | 30 | | | | | 35 | |

| Arg | Ile | Ser | Leu | Asp | Glu | Met | Val | Tyr | Lys | Ala | Ser |
| | | | 40 | | | | | 45 | | | |

| Asp | Ile | Val | Ile | Asn | Asn | Leu | Gly | Ala | Thr | Pro | Glu |
| | 50 | | | | | 55 | | | | | 60 |

| Gln | Ala | Lys | Arg | His | Lys | Asp | Ala | Val | Glu | Ala | Phe |
| | | | | 65 | | | | | 70 | | |

| Phe | Gly | Gly | Ala | Gly | Met | Lys | Tyr | Gly | Val | Glu | Thr |
| | | 75 | | | | | 80 | | | | |

| Glu | Trp | Pro | Glu | Tyr | Ile | Glu | Gly | Trp | Lys | Arg | Leu |
| 85 | | | | | 90 | | | | | 95 | |

| Ala | Ser | Glu | Glu | Leu | Lys | Arg | Tyr | Ser | Lys | Asn | Gln |
| | | | 100 | | | | | 105 | | | |

| Ile | Thr | Leu | Ile | Arg | Leu | Trp | Gly | Asp | Ala | Leu | Phe |
| | 110 | | | | | 115 | | | | | 120 |

| Asp | Ile | Ile | Ser | Lys | Asp | Gln | Asn | Gly | Ala | Ile | Ser |
| | | | | 125 | | | | | 130 | | |

| Leu | Asp | Glu | Trp | Lys | Ala | Tyr | Thr | Lys | Ser | Ala | Gly |
| | | 135 | | | | | 140 | | | | |

| Ile | Ile | Gln | Ser | Ser | Glu | Asp | Cys | Glu | Glu | Thr | Phe |
| 145 | | | | | 150 | | | | | 155 | |

| Arg | Val | Cys | Asp | Ile | Asp | Glu | Ser | Gly | Gln | Leu | Asp |
| | | | 160 | | | | | 165 | | | |

| Val | Asp | Glu | Met | Thr | Arg | Gln | His | Leu | Gly | Phe | Trp |
| | 170 | | | | | 175 | | | | | 180 |

| Tyr | Thr | Met | Asp | Pro | Ala | Cys | Glu | Lys | Leu | Tyr | Gly |
| | | | | 185 | | | | | 190 | | |

| Gly | Ala | Val | Pro |
| | | 195 | |

( 2 ) INFORMATION FOR SEQ ID NO: 4:

( i ) SEQUENCE CHARACTERISTICS:
        ( A ) LENGTH: 196 amino acids
        ( B ) TYPE: amino acid
        ( D ) TOPOLOGY: linear ( i i ) MOLECULE TYPE: protein ( i x ) FEATURE:
        ( A ) NAME/KEY: Recombinant site- directed aequorin mutant
        ( D ) OTHER INFORMATION: Site- directed aequorin mutant having
            increased bioluminescent activity ( x ) PUBLICATION INFORMATION:
        ( K ) RELEVANT RESIDUES IN SEQ ID NO: 4: Glu 135 changed to Ser ( x i ) SEQUENCE DESCRIPTION: SEQ ID NO: 4:

| Met | Thr | Ser | Glu | Gln | Tyr | Ser | Val | Lys | Leu | Thr | Pro |
| 1 | | | | 5 | | | | | 10 | | |

| Asp | Phe | Asp | Asn | Pro | Lys | Trp | Ile | Gly | Arg | His | Lys |
| | | 15 | | | | | 20 | | | | |

| His | Met | Phe | Asn | Phe | Leu | Asp | Val | Asn | His | Asn | Gly |
| 25 | | | | | 30 | | | | | 35 | |

| | | | | | | | | | | |
|---|---|---|---|---|---|---|---|---|---|---|
| Arg | Ile | Ser | Leu<br>40 | Asp | Glu | Met | Val | Tyr<br>45 | Lys | Ala | Ser |
| Asp | Ile<br>50 | Val | Ile | Asn | Asn | Leu<br>55 | Gly | Ala | Thr | Pro | Glu<br>60 |
| Gln | Ala | Lys | Arg | His<br>65 | Lys | Asp | Ala | Val | Glu<br>70 | Ala | Phe |
| Phe | Gly | Gly<br>75 | Ala | Gly | Met | Lys | Tyr<br>80 | Gly | Val | Glu | Thr |
| Glu<br>85 | Trp | Pro | Glu | Tyr | Ile<br>90 | Glu | Gly | Trp | Lys | Arg<br>95 | Leu |
| Ala | Ser | Glu | Glu<br>100 | Leu | Lys | Arg | Tyr | Ser<br>105 | Lys | Asn | Gln |
| Ile | Thr<br>110 | Leu | Ile | Arg | Leu | Trp<br>115 | Gly | Asp | Ala | Leu | Phe<br>120 |
| Asp | Ile | Ile | Asp | Lys<br>125 | Asp | Gln | Asn | Gly | Ala<br>130 | Ile | Ser |
| Leu | Asp | Ser<br>135 | Trp | Lys | Ala | Tyr | Thr<br>140 | Lys | Ser | Ala | Gly |
| Ile<br>145 | Ile | Gln | Ser | Ser | Glu<br>150 | Asp | Cys | Glu | Glu | Thr<br>155 | Phe |
| Arg | Val | Cys | Asp<br>160 | Ile | Asp | Glu | Ser | Gly<br>165 | Gln | Leu | Asp |
| Val | Asp<br>170 | Glu | Met | Thr | Arg | Gln<br>175 | His | Leu | Gly | Phe | Trp<br>180 |
| Tyr | Thr | Met | Asp | Pro<br>185 | Ala | Cys | Glu | Lys | Leu<br>190 | Tyr | Gly |
| Gly | Ala | Val<br>195 | Pro | | | | | | | | |

( 2 ) INFORMATION FOR SEQ ID NO: 5:

( i ) SEQUENCE CHARACTERISTICS:
            ( A ) LENGTH: 196 amino acids
            ( B ) TYPE: amino acid
            ( D ) TOPOLOGY: linear ( i i ) MOLECULE TYPE: protein ( i x ) FEATURE:
            ( A ) NAME/KEY: Recombinant site- directed acquorin mutant
            ( D ) OTHER INFORMATION: Site- directed mutant having increased
                  bioluminescent activity ( x ) PUBLICATION INFORMATION:
            ( K ) RELEVANT RESIDUES IN SEQ ID NO: 5: Gly 129 changed to Ala ( x i ) SEQUENCE DESCRIPTION: SEQ ID NO: 5:

| | | | | | | | | | | |
|---|---|---|---|---|---|---|---|---|---|---|
| Met<br>1 | Thr | Ser | Glu | Gln<br>5 | Tyr | Ser | Val | Lys | Leu<br>10 | Thr | Pro |
| Asp | Phe | Asp<br>15 | Asn | Pro | Lys | Trp | Ile<br>20 | Gly | Arg | His | Lys |
| His<br>25 | Met | Phe | Asn | Phe | Leu<br>30 | Asp | Val | Asn | His<br>35 | Asn | Gly |
| Arg | Ile | Ser | Leu<br>40 | Asp | Glu | Met | Val | Tyr<br>45 | Lys | Ala | Ser |
| Asp | Ile<br>50 | Val | Ile | Asn | Asn | Leu<br>55 | Gly | Ala | Thr | Pro | Glu<br>60 |
| Gln | Ala | Lys | Arg | His<br>65 | Lys | Asp | Ala | Val | Glu<br>70 | Ala | Phe |

| | | | | | | | | | | |
|---|---|---|---|---|---|---|---|---|---|---|
| Phe | Gly | Gly<br>75 | Ala | Gly | Met | Lys | Tyr<br>80 | Gly | Val | Glu | Thr |
| Glu<br>85 | Trp | Pro | Glu | Tyr | Ile<br>90 | Glu | Gly | Trp | Lys | Arg<br>95 | Leu |
| Ala | Ser | Glu | Glu<br>100 | Leu | Lys | Arg | Tyr | Ser<br>105 | Lys | Asn | Gln |
| Ile | Thr<br>110 | Leu | Ile | Arg | Leu | Trp<br>115 | Gly | Asp | Ala | Leu | Phe<br>120 |
| Asp | Ile | Ile | Asp | Lys<br>125 | Asp | Gln | Asn | Ala | Ala<br>130 | Ile | Ser |
| Leu | Asp | Glu<br>135 | Trp | Lys | Ala | Tyr | Thr<br>140 | Lys | Ser | Ala | Gly |
| Ile<br>145 | Ile | Gln | Ser | Ser | Glu<br>150 | Asp | Cys | Glu | Glu | Thr<br>155 | Phe |
| Arg | Val | Cys | Asp<br>160 | Ile | Asp | Glu | Ser | Gly<br>165 | Gln | Leu | Asp |
| Val | Asp<br>170 | Glu | Met | Thr | Arg | Gln<br>175 | His | Leu | Gly | Phe | Trp<br>180 |
| Tyr | Thr | Met | Asp | Pro<br>185 | Ala | Cys | Glu | Lys | Leu<br>190 | Tyr | Gly |
| Gly | Ala | Val<br>195 | Pro | | | | | | | | |

( 2 ) INFORMATION FOR SEQ ID NO: 6:

( i ) SEQUENCE CHARACTERISTICS:
        ( A ) LENGTH: 588 base pairs
        ( B ) TYPE: nucleic acid
        ( C ) STRANDEDNESS: Double stranded
        ( D ) TOPOLOGY: linear ( i i ) MOLECULE TYPE: genomic DNA ( i x ) FEATURE:
        ( A ) NAME/KEY: Recombinant Aequorin
        ( D ) OTHER INFORMATION: Codes for bioluminescent protein ( x ) PUBLICATION INFORMATION:
        ( A ) AUTHORS: Prasher et al.
        ( B ) TITLE: Sequence Comparisons of Complementary DNAs
            Encoding
            Aequorin Isotypes
        ( C ) JOURNAL: Biochemistry
        ( D ) VOLUME: 26
        ( F ) PAGES: 1326-1332
        ( G ) DATE: 1987
        ( K ) RELEVANT RESIDUES IN SEQ ID NO: 6: Points of
            microheterogeneity where specific amino acid
            replacements may occur and still retain bioluminescent
            activity in the protein are residues: 4, 12, 15, 18, 37
            70, 71 85 88, 95, 98, 99, 102, 103, 105, 108, 109, 114,
            123, 132, 142, 148, 157, and 164.

( x i ) SEQUENCE DESCRIPTION: SEQ ID NO: 6:

| | | | | | | | | | | | |
|---|---|---|---|---|---|---|---|---|---|---|---|
| ATG | ACC | AGC | GAA | CAA | TAC | TCA | GTC | AAG | CTT | ACA | CCA | 36 |
| Met<br>1 | Thr | Ser | Glu | Gln<br>5 | Tyr | Ser | Val | Lys | Leu<br>10 | Thr | Pro |
| GAC | TTC | GAC | AAC | CCA | AAA | TGG | ATT | GGA | CGA | CAC | AAG | 72 |
| Asp | Phe | Asp<br>15 | Asn | Pro | Lys | Trp | Ile<br>20 | Gly | Arg | His | Lys |
| CAC | ATG | TTT | AAT | TTT | CTT | GAT | GTC | AAC | CAC | AAT | GGA | 108 |
| His<br>25 | Met | Phe | Asn | Phe | Leu<br>30 | Asp | Val | Asn | His | Asn<br>35 | Gly |
| AGG | ATC | TCT | CTT | GAC | GAG | ATG | GTC | TAC | AAG | GCG | TCC | 144 |
| Arg | Ile | Ser | Leu | Asp | Glu | Met | Val | Tyr | Lys | Ala | Ser |

|     |     |     | 40  |     |     |     |     |     | 45  |     |     |     |
|-----|-----|-----|-----|-----|-----|-----|-----|-----|-----|-----|-----|-----|
| GAT | ATT | GTT | ATA | AAC | AAT | CTT | GGA | GCA | ACA | CCT | GAA | 180 |
| Asp | Ile | Val | Ile | Asn | Asn | Leu | Gly | Ala | Thr | Pro | Glu |     |
|     | 50  |     |     |     | 55  |     |     |     |     | 60  |     |     |
| CAA | GCC | AAA | CGT | CAC | AAA | GAT | GCT | GTA | GAA | GCC | TTC | 216 |
| Gln | Ala | Lys | Arg | His | Lys | Asp | Ala | Val | Glu | Ala | Phe |     |
|     |     |     |     | 65  |     |     |     |     | 70  |     |     |     |
| TTC | GGA | GGA | GCT | GCA | ATG | AAA | TAT | GGT | GTA | GAA | ACT | 252 |
| Phe | Gly | Gly | Ala | Gly | Met | Lys | Tyr | Gly | Val | Glu | Thr |     |
|     |     | 75  |     |     |     |     | 80  |     |     |     |     |     |
| GAA | TGG | CCT | GAA | TAC | ATC | GAA | GGA | TGG | AAA | AGA | CTG | 288 |
| Glu | Trp | Pro | Glu | Tyr | Ile | Glu | Gly | Trp | Lys | Arg | Leu |     |
| 85  |     |     |     |     | 90  |     |     |     | 95  |     |     |     |
| GCT | TCC | GAG | GAA | TTG | AAA | AGG | TAT | TCA | AAA | AAC | CAA | 324 |
| Ala | Ser | Glu | Glu | Leu | Lys | Arg | Tyr | Ser | Lys | Asn | Gln |     |
|     |     |     | 100 |     |     |     |     | 105 |     |     |     |     |
| ATC | ACA | CTT | ATT | CGT | TTA | TGG | GGT | GAT | GCA | TTG | TTC | 360 |
| Ile | Thr | Leu | Ile | Arg | Leu | Trp | Gly | Asp | Ala | Leu | Phe |     |
|     | 110 |     |     |     |     | 115 |     |     |     |     | 120 |     |
| GAT | ATC | ATT | GAC | AAA | GAC | CAA | AAT | GGA | GCT | ATT | TCA | 396 |
| Asp | Ile | Ile | Asp | Lys | Asp | Gln | Asn | Gly | Ala | Ile | Ser |     |
|     |     |     |     | 125 |     |     |     |     |     | 130 |     |     |
| CTG | GAT | GAA | TGG | AAA | GCA | TAC | ACC | AAA | TCT | GCT | GGC | 432 |
| Leu | Asp | Glu | Trp | Lys | Ala | Tyr | Thr | Lys | Ser | Ala | Gly |     |
|     |     | 135 |     |     |     |     | 140 |     |     |     |     |     |
| ATC | ATC | CAA | TCG | TCA | GAA | GAT | TGC | GAG | GAA | ACA | TTC | 468 |
| Ile | Ile | Gln | Ser | Ser | Glu | Asp | Cys | Glu | Glu | Thr | Phe |     |
| 145 |     |     |     |     | 150 |     |     |     |     | 155 |     |     |
| AGA | GTG | TGC | GAT | ATT | GAT | GAA | AGT | GGA | CAG | CTC | GAT | 504 |
| Arg | Val | Cys | Asp | Ile | Asp | Glu | Ser | Gly | Gln | Leu | Asp |     |
|     |     |     | 160 |     |     |     |     | 165 |     |     |     |     |
| GTT | GAT | GAG | ATG | ACA | AGA | CAA | CAT | TTA | GGA | TTT | TGG | 540 |
| Val | Asp | Glu | Met | Thr | Arg | Gln | His | Leu | Gly | Phe | Trp |     |
|     | 170 |     |     |     |     | 175 |     |     |     |     | 180 |     |
| TAC | ACC | ATG | GAT | CCT | GCT | TGC | GAA | AAG | CTC | TAC | GGT | 576 |
| Tyr | Thr | Met | Asp | Pro | Ala | Cys | Glu | Lys | Leu | Tyr | Gly |     |
|     |     |     |     | 185 |     |     |     |     | 190 |     |     |     |
| GGA | GCT | GTC | CCC | 588 |     |     |     |     |     |     |     |     |
| Gly | Ala | Val | Pro |     |     |     |     |     |     |     |     |     |
|     |     | 195 |     |     |     |     |     |     |     |     |     |     |

( 2 ) INFORMATION FOR SEQ ID NO: 7:

( i ) SEQUENCE CHARACTERISTICS:
                ( A ) LENGTH: 567 base pairs
                ( B ) TYPE: nucleic acid
                ( C ) STRANDEDNESS: Double stranded
                ( D ) TOPOLOGY: linear ( i i ) MOLECULE TYPE: genomic DNA ( i x ) FEATURE:
                ( A ) NAME/KEY: Recombinant Aequorin
                ( D ) OTHER INFORMATION: Code for bioluminescent protein ( x ) PUBLICATION INFORMATION:
                ( A ) AUTHORS: Charbonneau et al.
                ( B ) TITLE: Amino acid sequence of the calcium-dependent
                      photoprotein aequorin
                ( C ) JOURNAL: Am. Chem. Soc.
                ( D ) VOLUME: 24
                ( E ) ISSUE: 24
                ( F ) PAGES: 6762-6771
                ( G ) DATE: 1985
                ( K ) RELEVANT RESIDUES IN SEQ ID NO: 7: Points of
                      microheterogeneity where specific amino acid replacements may occur and still retain bioluminescent activity in the protein are residues: 12, 15, 18, 37, 70, 71, 85, 88, 95, 98, 99, 102, 103, 105, 108, 109, 114, 123, 132, 142, 148, 157, and 164.

( x i ) SEQUENCE DESCRIPTION: SEQ ID NO: 7:

| GTC | AAG | CTT | ACA | CCA | GAC | TTC | GAC | AAC | CCA | AAA | TGG | 36 |
| Val | Lys | Leu | Thr | Pro | Asp | Phe | Asp | Asn | Pro | Lys | Trp | |
| 1 | | | | 5 | | | | | 10 | | | |

| ATT | GGA | CGA | CAC | AAG | CAC | ATG | TTT | AAT | TTT | CTT | GAT | 72 |
| Ile | Gly | Arg | His | Lys | His | Met | Phe | Asn | Phe | Leu | Asp | |
| | | 15 | | | | 20 | | | | | | |

| GTC | AAC | CAC | AAT | GGA | AGG | ATC | TCT | CTT | GAC | GAG | ATG | 108 |
| Val | Asn | His | Asn | Gly | Arg | Ile | Ser | Leu | Asp | Glu | Met | |
| 25 | | | | | 30 | | | | | 35 | | |

| GTC | TAC | AAG | GCG | TCC | GAT | ATT | GTT | ATA | AAC | AAT | CTT | 144 |
| Val | Tyr | Lys | Ala | Ser | Asp | Ile | Val | Ile | Asn | Asn | Leu | |
| | | | 40 | | | | | 45 | | | | |

| GGA | GCA | ACA | CCT | GAA | CAA | GCC | AAA | CGT | CAC | AAA | GAT | 180 |
| Gly | Ala | Thr | Pro | Glu | Gln | Ala | Lys | Arg | His | Lys | Asp | |
| | 50 | | | | | 55 | | | | | 60 | |

| GCT | GTA | GAA | GCC | TTC | TTC | GGA | GGA | GCT | GCA | ATG | AAA | 216 |
| Ala | Val | Glu | Ala | Phe | Phe | Gly | Gly | Ala | Gly | Met | Lys | |
| | | | | 65 | | | | | 70 | | | |

| TAT | GGT | GTA | GAA | ACT | GAA | TGG | CCT | GAA | TAC | ATC | GAA | 252 |
| Tyr | Gly | Val | Glu | Thr | Glu | Trp | Pro | Glu | Tyr | Ile | Glu | |
| | | 75 | | | | | 80 | | | | | |

| GGA | TGG | AAA | AGA | CTG | GCT | TCC | GAG | GAA | TTG | AAA | AGG | 288 |
| Gly | Trp | Lys | Arg | Leu | Ala | Ser | Glu | Glu | Leu | Lys | Arg | |
| 85 | | | | | 90 | | | | | 95 | | |

| TAT | TCA | AAA | AAC | CAA | ATC | ACA | CTT | ATT | CGT | TTA | TGG | 324 |
| Tyr | Ser | Lys | Asn | Gln | Ile | Thr | Leu | Ile | Arg | Leu | Trp | |
| | | | 100 | | | | | 105 | | | | |

| GGT | GAT | GCA | TTG | TTC | GAT | ATC | ATT | GAC | AAA | GAC | CAA | 360 |
| Gly | Asp | Ala | Leu | Phe | Asp | Ile | Ile | Asp | Lys | Asp | Gln | |
| | 110 | | | | | 115 | | | | | 120 | |

| AAT | GGA | GCT | ATT | TCA | CTG | GAT | GAA | TGG | AAA | GCA | TAC | 396 |
| Asn | Gly | Ala | Ile | Ser | Leu | Asp | Glu | Trp | Lys | Ala | Tyr | |
| | | | | 125 | | | | | 130 | | | |

| ACC | AAA | TCT | GCT | GGC | ATC | ATC | CAA | TCG | TCA | GAA | GAT | 432 |
| Thr | Lys | Ser | Ala | Gly | Ile | Ile | Gln | Ser | Ser | Glu | Asp | |
| | | 135 | | | | | 140 | | | | | |

| TGC | GAG | GAA | ACA | TTC | AGA | GTG | TGC | GAT | ATT | GAT | GAA | 468 |
| Cys | Glu | Glu | Thr | Phe | Arg | Val | Cys | Asp | Ile | Asp | Glu | |
| 145 | | | | | 150 | | | | | 155 | | |

| AGT | GGA | CAG | CTC | GAT | GTT | GAT | GAG | ATG | ACA | AGA | CAA | 504 |
| Ser | Gly | Gln | Leu | Asp | Val | Asp | Glu | Met | Thr | Arg | Gln | |
| | | | 160 | | | | | 165 | | | | |

| CAT | TTA | GGA | TTT | TGG | TAC | ACC | ATG | GAT | CCT | GCT | TGC | 540 |
| His | Leu | Gly | Phe | Trp | Tyr | Thr | Met | Asp | Pro | Ala | Cys | |
| | 170 | | | | | 175 | | | | | 180 | |

| GAA | AAG | CTC | TAC | GGT | GGA | GCT | GTC | CCC | | | | 567 |
| Glu | Lys | Leu | Tyr | Gly | Gly | Ala | Val | Pro | | | | |
| | | | | 185 | | | | | | | | |

( 2 ) INFORMATION FOR SEQ ID NO: 8:

( i ) SEQUENCE CHARACTERISTICS:
        ( A ) LENGTH: 588 base pairs
        ( B ) TYPE: nucleic acid
        ( C ) STRANDEDNESS: Double stranded
        ( D ) TOPOLOGY: linear ( i i ) MOLECULE TYPE: genomic DNA ( i x ) FEATURE:
    ( A ) NAME/KEY: Recombinant site- directed aequorin mutant
    ( D ) OTHER INFORMATION: Site- directed mutant having increased bioluminescent activity.

( x ) PUBLICATION INFORMATION:
    ( K ) RELEVANT RESIDUES IN SEQ ID NO: 8: Asp 124 changed to Ser ( x i ) SEQUENCE DESCRIPTION: SEQ ID NO: 8:

| ATG | ACC | AGC | GAA | CAA | TAC | TCA | GTC | AAG | CTT | ACA | CCA | 36 |
|---|---|---|---|---|---|---|---|---|---|---|---|---|
| Met | Thr | Ser | Glu | Gln | Tyr | Ser | Val | Lys | Leu | Thr | Pro | |
| 1 | | | | 5 | | | | | 10 | | | |

| GAC | TTC | GAC | AAC | CCA | AAA | TGG | ATT | GGA | CGA | CAC | AAG | 72 |
|---|---|---|---|---|---|---|---|---|---|---|---|---|
| Asp | Phe | Asp | Asn | Pro | Lys | Trp | Ile | Gly | Arg | His | Lys | |
| | | 15 | | | | | 20 | | | | | |

| CAC | ATG | TTT | AAT | TTT | CTT | GAT | GTC | AAC | CAC | AAT | GGA | 108 |
|---|---|---|---|---|---|---|---|---|---|---|---|---|
| His | Met | Phe | Asn | Phe | Leu | Asp | Val | Asn | His | Asn | Gly | |
| 25 | | | | | 30 | | | | | 35 | | |

| AGG | ATC | TCT | CTT | GAC | GAG | ATG | GTC | TAC | AAG | GCG | TCC | 144 |
|---|---|---|---|---|---|---|---|---|---|---|---|---|
| Arg | Ile | Ser | Leu | Asp | Glu | Met | Val | Tyr | Lys | Ala | Ser | |
| | | | 40 | | | | | 45 | | | | |

| GAT | ATT | GTT | ATA | AAC | AAT | CTT | GGA | GCA | ACA | CCT | GAA | 180 |
|---|---|---|---|---|---|---|---|---|---|---|---|---|
| Asp | Ile | Val | Ile | Asn | Asn | Leu | Gly | Ala | Thr | Pro | Glu | |
| | 50 | | | | 55 | | | | | | 60 | |

| CAA | GCC | AAA | CGT | CAC | AAA | GAT | GCT | GTA | GAA | GCC | TTC | 216 |
|---|---|---|---|---|---|---|---|---|---|---|---|---|
| Gln | Ala | Lys | Arg | His | Lys | Asp | Ala | Val | Glu | Ala | Phe | |
| | | | | 65 | | | | | 70 | | | |

| TTC | GGA | GGA | GCT | GCA | ATG | AAA | TAT | GGT | GTA | GAA | ACT | 252 |
|---|---|---|---|---|---|---|---|---|---|---|---|---|
| Phe | Gly | Gly | Ala | Gly | Met | Lys | Tyr | Gly | Val | Glu | Thr | |
| | | 75 | | | | | 80 | | | | | |

| GAA | TGG | CCT | GAA | TAC | ATC | GAA | GGA | TGG | AAA | AGA | CTG | 288 |
|---|---|---|---|---|---|---|---|---|---|---|---|---|
| Glu | Trp | Pro | Glu | Tyr | Ile | Glu | Gly | Trp | Lys | Arg | Leu | |
| 85 | | | | | 90 | | | | | 95 | | |

| GCT | TCC | GAG | GAA | TTG | AAA | AGG | TAT | TCA | AAA | AAC | CAA | 324 |
|---|---|---|---|---|---|---|---|---|---|---|---|---|
| Ala | Ser | Glu | Glu | Leu | Lys | Arg | Tyr | Ser | Lys | Asn | Gln | |
| | | | 100 | | | | | 105 | | | | |

| ATC | ACA | CTT | ATT | CGT | TTA | TGG | GGT | GAT | GCA | TTG | TTC | 360 |
|---|---|---|---|---|---|---|---|---|---|---|---|---|
| Ile | Thr | Leu | Ile | Arg | Leu | Trp | Gly | Asp | Ala | Leu | Phe | |
| | 110 | | | | | 115 | | | | | 120 | |

| GAT | ATC | ATT | TCC | AAA | GAC | CAA | AAT | GGA | GCT | ATT | TCA | 396 |
|---|---|---|---|---|---|---|---|---|---|---|---|---|
| Asp | Ile | Ile | Ser | Lys | Asp | Gln | Asn | Gly | Ala | Ile | Ser | |
| | | | | 125 | | | | | 130 | | | |

| CTG | GAT | GAA | TGG | AAA | GCA | TAC | ACC | AAA | TCT | GCT | GGC | 432 |
|---|---|---|---|---|---|---|---|---|---|---|---|---|
| Leu | Asp | Glu | Trp | Lys | Ala | Tyr | Thr | Lys | Ser | Ala | Gly | |
| | | 135 | | | | | 140 | | | | | |

| ATC | ATC | CAA | TCG | TCA | GAA | GAT | TGC | GAG | GAA | ACA | TTC | 468 |
|---|---|---|---|---|---|---|---|---|---|---|---|---|
| Ile | Ile | Gln | Ser | Ser | Glu | Asp | Cys | Glu | Glu | Thr | Phe | |
| 145 | | | | | 150 | | | | | 155 | | |

| AGA | GTG | TGC | GAT | ATT | GAT | GAA | AGT | GGA | CAG | CTC | GAT | 504 |
|---|---|---|---|---|---|---|---|---|---|---|---|---|
| Arg | Val | Cys | Asp | Ile | Asp | Glu | Ser | Gly | Gln | Leu | Asp | |
| | | | 160 | | | | | 165 | | | | |

| GTT | GAT | GAG | ATG | ACA | AGA | CAA | CAT | TTA | GGA | TTT | TGG | 540 |
|---|---|---|---|---|---|---|---|---|---|---|---|---|
| Val | Asp | Glu | Met | Thr | Arg | Gln | His | Leu | Gly | Phe | Trp | |
| | 170 | | | | | 175 | | | | | 180 | |

| TAC | ACC | ATG | GAT | CCT | GCT | TGC | GAA | AAG | CTC | TAC | GGT | 576 |
|---|---|---|---|---|---|---|---|---|---|---|---|---|
| Tyr | Thr | Met | Asp | Pro | Ala | Cys | Glu | Lys | Leu | Tyr | Gly | |
| | | | | 185 | | | | | 190 | | | |

| GGA | GCT | GTC | CCC | 588 |
|---|---|---|---|---|
| Gly | Ala | Val | Pro | |
| | | 195 | | |

( 2 ) INFORMATION FOR SEQ ID NO: 9:

( i ) SEQUENCE CHARACTERISTICS:
        ( A ) LENGTH: 588 base pairs
        ( B ) TYPE: nucleic acid
        ( C ) STRANDEDNESS: Double stranded
        ( D ) TOPOLOGY: linear ( i i ) MOLECULE TYPE: genomic DNA ( i x ) FEATURE:
        ( A ) NAME/KEY: Recombinant site- directed aequorin mutant
        ( D ) OTHER INFORMATION: Site- directed aequorin mutant having
            increased bioluminescent activity ( x ) PUBLICATION INFORMATION:
        ( K ) RELEVANT RESIDUES IN SEQ ID NO: 9: Glu 135 changed to Ser ( x i ) SEQUENCE DESCRIPTION: SEQ ID NO: 9:

```
ATG  ACC  AGC  GAA  CAA  TAC  TCA  GTC  AAG  CTT  ACA  CCA      36
Met  Thr  Ser  Glu  Gln  Tyr  Ser  Val  Lys  Leu  Thr  Pro
 1              5                        10

GAC  TTC  GAC  AAC  CCA  AAA  TGG  ATT  GGA  CGA  CAC  AAG      72
Asp  Phe  Asp  Asn  Pro  Lys  Trp  Ile  Gly  Arg  His  Lys
         15                        20

CAC  ATG  TTT  AAT  TTT  CTT  GAT  GTC  AAC  CAC  AAT  GGA     108
His  Met  Phe  Asn  Phe  Leu  Asp  Val  Asn  His  Asn  Gly
25                        30                        35

AGG  ATC  TCT  CTT  GAC  GAG  ATG  GTC  TAC  AAG  GCG  TCC     144
Arg  Ile  Ser  Leu  Asp  Glu  Met  Val  Tyr  Lys  Ala  Ser
              40                        45

GAT  ATT  GTT  ATA  AAC  AAT  CTT  GGA  GCA  ACA  CCT  GAA     180
Asp  Ile  Val  Ile  Asn  Asn  Leu  Gly  Ala  Thr  Pro  Glu
         50                        55                        60

CAA  GCC  AAA  CGT  CAC  AAA  GAT  GCT  GTA  GAA  GCC  TTC     216
Gln  Ala  Lys  Arg  His  Lys  Asp  Ala  Val  Glu  Ala  Phe
                   65                        70

TTC  GGA  GGA  GCT  GCA  ATG  AAA  TAT  GGT  GTA  GAA  ACT     252
Phe  Gly  Gly  Ala  Gly  Met  Lys  Tyr  Gly  Val  Glu  Thr
              75                        80

GAA  TGG  CCT  GAA  TAC  ATC  GAA  GGA  TGG  AAA  AGA  CTG     288
Glu  Trp  Pro  Glu  Tyr  Ile  Glu  Gly  Trp  Lys  Arg  Leu
85                        90                        95

GCT  TCC  GAG  GAA  TTG  AAA  AGG  TAT  TCA  AAA  AAC  CAA     324
Ala  Ser  Glu  Glu  Leu  Lys  Arg  Tyr  Ser  Lys  Asn  Gln
                  100                       105

ATC  ACA  CTT  ATT  CGT  TTA  TGG  GGT  GAT  GCA  TTG  TTC     360
Ile  Thr  Leu  Ile  Arg  Leu  Trp  Gly  Asp  Ala  Leu  Phe
         110                       115                      120

GAT  ATC  ATT  TCC  AAA  GAC  CAA  AAT  GGA  GCT  ATT  TCA     396
Asp  Ile  Ile  Ser  Lys  Asp  Gln  Asn  Gly  Ala  Ile  Ser
                  125                       130

CTG  GAT  TCA  TGG  AAA  GCA  TAC  ACC  AAA  TCT  GCT  GGC     432
Leu  Asp  Ser  Trp  Lys  Ala  Tyr  Thr  Lys  Ser  Ala  Gly
         135                       140

ATC  ATC  CAA  TCG  TCA  GAA  GAT  TGC  GAG  GAA  ACA  TTC     468
Ile  Ile  Gln  Ser  Ser  Glu  Asp  Cys  Glu  Glu  Thr  Phe
145                       150                       155

AGA  GTG  TGC  GAT  ATT  GAT  GAA  AGT  GGA  CAG  CTC  GAT     504
Arg  Val  Cys  Asp  Ile  Asp  Glu  Ser  Gly  Gln  Leu  Asp
                  160                       165

GTT  GAT  GAG  ATG  ACA  AGA  CAA  CAT  TTA  GGA  TTT  TGG     540
Val  Asp  Glu  Met  Thr  Arg  Gln  His  Leu  Gly  Phe  Trp
```

```
                 170                         175                         180
TAC   ACC   ATG   GAT   CCT   GCT   TGC   GAA   AAG   CTC   TAC   GGT       576
Tyr   Thr   Met   Asp   Pro   Ala   Cys   Glu   Lys   Leu   Tyr   Gly
                        185                           190

GGA   GCT   GTC   CCC                                                       588
Gly   Ala   Val   Pro
            195
```

( 2 ) INFORMATION FOR SEQ ID NO: 10:

( i ) SEQUENCE CHARACTERISTICS:
        ( A ) LENGTH: 588 base pairs
        ( B ) TYPE: nucleic acid
        ( C ) STRANDEDNESS: Double stranded
        ( D ) TOPOLOGY: linear ( i i ) MOLECULE TYPE: genomic DNA ( i x ) FEATURE:
        ( A ) NAME/KEY: Recombinant site- directed aequorin mutant
        ( D ) OTHER INFORMATION: Site- directed mutant having increased
            bioluminescent activity ( x ) PUBLICATION INFORMATION:
        ( K ) RELEVANT RESIDUES IN SEQ ID NO: 10: Gly 129 changed to Ala ( x i ) SEQUENCE DESCRIPTION: SEQ ID NO: 10:

```
ATG   ACC   AGC   GAA   CAA   TAC   TCA   GTC   AAG   CTT   ACA   CCA        36
Met   Thr   Ser   Glu   Gln   Tyr   Ser   Val   Lys   Leu   Thr   Pro
1                       5                             10

GAC   TTC   GAC   AAC   CCA   AAA   TGG   ATT   GGA   CGA   CAC   AAG        72
Asp   Phe   Asp   Asn   Pro   Lys   Trp   Ile   Gly   Arg   His   Lys
                  15                        20

CAC   ATG   TTT   AAT   TTT   CTT   GAT   GTC   AAC   CAC   AAT   GGA       108
His   Met   Phe   Asn   Phe   Leu   Asp   Val   Asn   His   Asn   Gly
25                            30                                35

AGG   ATC   TCT   CTT   GAC   GAG   ATG   GTC   TAC   AAG   GCG   TCC       144
Arg   Ile   Ser   Leu   Asp   Glu   Met   Val   Tyr   Lys   Ala   Ser
                  40                              45

GAT   ATT   GTT   ATA   AAC   AAT   CTT   GGA   GCA   ACA   CCT   GAA       180
Asp   Ile   Val   Ile   Asn   Asn   Leu   Gly   Ala   Thr   Pro   Glu
      50                              55                                60

CAA   GCC   AAA   CGT   CAC   AAA   GAT   GCT   GTA   GAA   GCC   TTC       216
Gln   Ala   Lys   Arg   His   Lys   Asp   Ala   Val   Glu   Ala   Phe
                        65                              70

TTC   GGA   GGA   GCT   GCA   ATG   AAA   TAT   GGT   GTA   GAA   ACT       252
Phe   Gly   Gly   Ala   Gly   Met   Lys   Tyr   Gly   Val   Glu   Thr
            75                              80

GAA   TGG   CCT   GAA   TAC   ATC   GAA   GGA   TGG   AAA   AGA   CTG       288
Glu   Trp   Pro   Glu   Tyr   Ile   Glu   Gly   Trp   Lys   Arg   Leu
85                              90                        95

GCT   TCC   GAG   GAA   TTG   AAA   AGG   TAT   TCA   AAA   AAC   CAA       324
Ala   Ser   Glu   Glu   Leu   Lys   Arg   Tyr   Ser   Lys   Asn   Gln
                  100                           105

ATC   ACA   CTT   ATT   CGT   TTA   TGG   GGT   GAT   GCA   TTG   TTC       360
Ile   Thr   Leu   Ile   Arg   Leu   Trp   Gly   Asp   Ala   Leu   Phe
      110                           115                                 120

GAT   ATC   ATT   TCC   AAA   GAC   CAA   AAT   GCA   GCT   ATT   TCA       396
Asp   Ile   Ile   Ser   Lys   Asp   Gln   Asn   Ala   Ala   Ile   Ser
                        125                             130

CTG   GAT   GAA   TGG   AAA   GCA   TAC   ACC   AAA   TCT   GCT   GGC       432
Leu   Asp   Glu   Trp   Lys   Ala   Tyr   Thr   Lys   Ser   Ala   Gly
            135                             140

ATC   ATC   CAA   TCG   TCA   GAA   GAT   TGC   GAG   GAA   ACA   TTC       468
```

| | | | | | | | | | | | | |
|---|---|---|---|---|---|---|---|---|---|---|---|---|
| Ile | Ile | Gln | Ser | Ser | Glu | Asp | Cys | Glu | Glu | Thr | Phe | |
| 145 | | | | | 150 | | | | | 155 | | |
| AGA | GTG | TGC | GAT | ATT | GAT | GAA | AGT | GGA | CAG | CTC | GAT | 504 |
| Arg | Val | Cys | Asp | Ile | Asp | Glu | Ser | Gly | Gln | Leu | Asp | |
| | | | 160 | | | | | 165 | | | | |
| GTT | GAT | GAG | ATG | ACA | AGA | CAA | CAT | TTA | GGA | TTT | TGG | 540 |
| Val | Asp | Glu | Met | Thr | Arg | Gln | His | Leu | Gly | Phe | Trp | |
| | 170 | | | | | 175 | | | | | 180 | |
| TAC | ACC | ATG | GAT | CCT | GCT | TGC | GAA | AAG | CTC | TAC | GGT | 576 |
| Tyr | Thr | Met | Asp | Pro | Ala | Cys | Glu | Lys | Leu | Tyr | Gly | |
| | | | | 185 | | | | | 190 | | | |
| GGA | GCT | GTC | CCC | 588 | | | | | | | | |
| Gly | Ala | Val | Pro | | | | | | | | | |
| | | 195 | | | | | | | | | | |

I claim:

1. A composition comprising an isolated altered apoaequorin DNA sequence, wherein at least the codon that codes for an aspartic acid at amino acid position 124 in the amino acid sequence of natural apoaequorin is changed to a codon that codes for serine, wherein said isolated altered apoaequorin DNA sequence codes for an altered apoaequorin which, when combined with a luciferin and a light-triggering cation, has greater bioluminescent activity than natural apoaequorin combined with a luciferin and a light-triggering cation.

2. The composition of claim 1 wherein the altered apoaequorin DNA is SEQ ID NO: 8.

3. A composition comprising an isolated altered apoaequorin DNA sequence, wherein at least the codon that codes for a glutamic acid at amino acid position 135 in the amino acid sequence of natural apoaequorin is changed to a codon that codes for serine, wherein said isolated altered apoaequorin DNA sequence codes for an altered apoaequorin which, when combined with a luciferin and a light-triggering cation, has greater bioluminescent activity than natural apoaequorin combined with a luciferin and a light-triggering cation.

4. The composition of claim 3 wherein the altered apoaequorin DNA is SEQ ID NO: 9.

5. A composition comprising an isolated altered apoaequorin DNA sequence, wherein at least the codon that codes for a glycine at amino acid position 129 in the amino acid sequence of natural apoaequorin is changed to a codon that codes for alanine, wherein said isolated altered apoaequorin DNA sequence codes for an altered apoaequorin which, when combined with a luciferin and a light-triggering cation, has greater bioluminescent activity than natural apoaequorin combined with a luciferin and a light-triggering cation.

6. The composition of claim 5 wherein the altered apoaequorin DNA is SEQ ID NO: 10.

7. A composition comprising an isolated, altered, apoaequorin DNA sequence, wherein at least the codon that codes for an aspartic acid at codon position 117 of SEQ ID NO: 7 is changed to a codon that codes for serine, wherein said isolated altered apoaequorin DNA sequence codes for an altered apoaequorin which, when combined with a luciferin and a light-triggering cation, has greater bioluminescent activity than natural apoaequorin combined with a luciferin and a light-triggering cation.

8. A composition comprising an isolated altered apoaequorin DNA sequence, wherein at least the codon that codes for a glutamic acid at codon position 128 of SEQ ID NO: 7 is changed to a codon that codes for serine, wherein said isolated altered apoaequorin DNA sequence codes for an altered apoaequorin which, when combined with a luciferin and a light-triggering cation, has greater bioluminescent activity than natural apoaequorin combined with a luciferin and a light-triggering cation.

9. A composition comprising an isolated altered apoaequorin DNA sequence, wherein at least the codon that codes for a glycine at codon position 122 of SEQ ID NO: 7 in the amino acid sequence of natural apoaequorin is changed to a codon that codes for alanine, wherein said isolated altered apoaequorin DNA sequence codes for an altered apoaequorin which, when combined with a luciferin and a light-triggering cation, has greater bioluminescent activity than natural apoaequorin combined with a luciferin and a light-triggering cation.

* * * * *